(12) United States Patent
Braun et al.

(10) Patent No.: US 10,112,932 B2
(45) Date of Patent: Oct. 30, 2018

(54) BENZOXAZEPIN OXAZOLIDINONE COMPOUNDS AND METHODS OF USE

(71) Applicant: Genentech, Inc., South San Francisco, CA (US)

(72) Inventors: Marie-Gabrielle Braun, South San Francisco, CA (US); Emily Hanan, Redwood City, CA (US); Steven T. Staben, San Francisco, CA (US); Robert Andrew Heald, Sawbridgeworth (GB); Calum MacLeod, Harlow Essex (GB); Richard Elliott, Harlow Essex (GB)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/729,507

(22) Filed: Oct. 10, 2017

(65) Prior Publication Data
US 2018/0127404 A1 May 10, 2018

Related U.S. Application Data

(63) Continuation of application No. 15/481,764, filed on Apr. 7, 2017, now abandoned, which is a continuation of application No. 15/200,301, filed on Jul. 1, 2016, now Pat. No. 9,650,393.

(60) Provisional application No. 62/188,029, filed on Jul. 2, 2015.

(51) Int. Cl.
| A61K 31/553 | (2006.01) |
| C07D 413/14 | (2006.01) |
| C07D 498/04 | (2006.01) |
| C07D 267/08 | (2006.01) |

(52) U.S. Cl.
CPC .......... *C07D 413/14* (2013.01); *A61K 31/553* (2013.01); *C07D 267/08* (2013.01); *C07D 498/04* (2013.01)

(58) Field of Classification Search
CPC .................................................. A61K 31/553
USPC ......................................................... 514/183
See application file for complete search history.

(56) References Cited

U.S. PATENT DOCUMENTS

| 8,242,104 | B2 * | 8/2012 | Blaquiere | C07D 498/04 514/211.1 |
| 8,263,633 | B2 | 9/2012 | Blaquiere et al. | |
| 8,343,955 | B2 | 1/2013 | Blaquiere et al. | |
| 8,586,574 | B2 | 11/2013 | Blaquiere et al. | |
| 8,785,626 | B2 | 7/2014 | Blaquiere et al. | |
| 9,107,926 | B2 | 8/2015 | Belvin et al. | |
| 9,271,988 | B2 | 3/2016 | Kim et al. | |
| 9,643,980 | B2 | 5/2017 | Braun et al. | |
| 9,650,393 | B2 | 5/2017 | Braun et al. | |
| 2014/0275523 | A1 | 9/2014 | Angelaud et al. | |
| 2013/0005706 | A1 | 1/2017 | Corkey et al. | |

FOREIGN PATENT DOCUMENTS

| WO | 2011/036280 A1 | 3/2011 |
| WO | 2011/036284 A1 | 3/2011 |
| WO | 2012/126901 A1 | 9/2012 |
| WO | 2013/182668 A1 | 12/2013 |
| WO | 2014/140073 A1 | 9/2014 |
| WO | 2017/001645 A1 | 1/2017 |
| WO | 2017/001658 A1 | 1/2017 |

OTHER PUBLICATIONS

Abraham Jane et al., "PI3K/AKT/mTOR pathway inhibitors: the ideal combination partners for breast cancer therapies?" Expert Review of Anticancer Therapy 15(1):51-68 (Oct. 11, 2014).
Akinleye et al., "Phosphatidylinositol 3-kinase (PI3K) inhibitors as cancer therapeutics" J Hematol Oncol. 6(1):88-105 (Nov. 22, 2013).
Bohm et al., "Flourine in medicinal chemistry" Chembiochem. 5(5):637-43 (May 3, 2004).
Castanedo et al., "Synthesis of Fused Imidazole-Containing Ring Systems via Dual Oxidative Amination of C(sp(3))-H Bonds" J Org Chem. 81(18):8617-24 (Sep. 16, 2016).
Chen et al., "Engineering of an isolated p110α sunbunit of PI3Kα permits crystallization and provides a platform for structure-based drug design" Protein Sci. 23(10):1332-40 (Oct. 2014).
Ciruelos Gil Eva Maria, "Targeting the PI3K/AKT/mTOR pathway in estrogen receptor-positive breast cancer" Cancer Treatment Reviews 40:862-871 (Aug. 2014).

(Continued)

*Primary Examiner* — Sun Jae Yoo
(74) *Attorney, Agent, or Firm* — Zong-Qiang Bill Tian

(57) ABSTRACT

Described herein are benzoxazepin oxazolidinone compounds with phosphoinositide-3 kinase (PI3K) modulation activity or function having the Formula I structure:

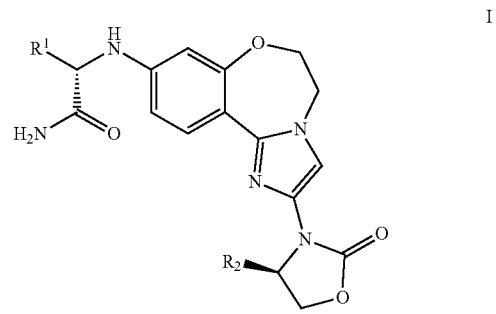

or stereoisomers, tautomers, or pharmaceutically acceptable salts thereof, and with the substituents and structural features described herein. Also described are pharmaceutical compositions and medicaments that include the Formula I compounds, as well as methods of using such PI3K modulators, alone and in combination with other therapeutic agents, for treating diseases or conditions that are mediated or dependent upon PI3K dysregulation. Also described are methods of making the benzoxazepin oxazolidinone compounds having the Formula I structure.

9 Claims, 4 Drawing Sheets

(56) References Cited

OTHER PUBLICATIONS

Notification of Transmittal of the International Search Report and the Written Opinion of the International Searching Authority, or the Declaration dated Aug. 22, 2016.

Edgar et al., "Amphiregulin and PTEN evoke a multimodal mechanism of acquried resistance to PI3L inhibition" Genes Cancer 5 (SUPPL 3-4):113-26 (2014).

Edgar et al., "Isoform-Specific Phosphoinositide 3-Kinase Inhibitors Exert Distinct Effects in Solid Tumors" Cancer RES 70(3):1164-1172 (Feb. 1, 2010).

Friedman et al., "Selective PI3K and dual PI3K/mTOR inhibitors enhance the efficacy of endocrine therapies in breast cancer models" Cancer RES-AACR San Antonio Breast Cancer Symposium (Abstract), 72(24 SUPPL3) (Dec. 4-8, 2012).

Heffron et al., "Rational design of phosphoinositide 3-kinase α inhibitors that exhibit selectivity over the phosphoinositide 3-kinase β isoform" J Med Chem. 54:7815-33 (2011).

Heffron et al., "Rational Design of Selective Benzoxazepin Inhibitors of the α-Isoform of Phosphoinositide 3-Kinase Culminating in the Identification of (S)-2-((2-(1-Isopropyl-1H-1,2,4-triazol-5-yl)-5,6-dihydrobenzo[f]imidazo[1,2-d][1,4]oxazepin-9-yl)oxy)propanamide (GDC-0326)" J Med Chem. 59(3):985-1002 (Feb. 11, 2016).

Herrera-Abreu, M.T. et al., "Early Adaptation and Acquried Resistance to CDK4/6 Inhibition in Estrogen Receptor-Positive Breast Cancer" Cancer Research 76(8):2301-2313 (2016).

Lopez et al., "Taselisib, a selective inhibitor of PIK3CA, is highly effective on PIK3CA-mutated and HER2/neuamplified uterine serous carcinoma in vitro and in vivo" Gynecol Oncol. 135(2):312-7 (Nov. 2014).

Lovering et al., "Escape from flatland: increasing saturation as an approach to improving clinical success" J Med Chem. 52(21):6752-6 (Nov. 12, 2009).

Nacht et al., "Discovery of a potent and isoform-selective targeted covalent inhibitor of the lipid kinase PI3Kα" J Med Chem. 56(3):712-21 (Feb. 14, 2013).

Nbudaku et al., "Discovery of 2-{3-[2-(1-Isopropyl-3-methyl-1H-1,2-4-triazol-5-yl)-5,6-dihydrobenzo[f]imidazo[1,2-d][1,4]oxazepin-9-yl]-1H-pyrazol-1-yl}-2-methylpropanamide (GDC-0032: A β-Sparing phosphoinositide 3-Kinase Inhibitors with High Unbound Exposure and Robust in Vivo Antitumor Activity" J Med Chem 56:4597-4610 (2013).

O'Brien et al., "Predictive Biomarkers of Sensitivity to the phosphatidylinositol 3 Kinase Inhibitor GDC-0941 in Breast Cancer Perclinical Models" Clin Cancer Res 16(14):3670-3683 (Jul. 15, 2010).

Ritchie et al., "Physicochemical discriptors of aromatic character and their use in drug recovery" J Med Chem. 57(14):7206-15 (Sep. 11, 2014).

Saura C et al., "Phase Ib Study of the PI3K Inhibitor Taselisib (GDC-0032) in Combination with Letrozole in Patients with Hormone Receptor-Positive Adavanced Breast Cancer-RD5-2" San Antonio Breast Cancer Symposium, (Dec. 12, 2014).

She et al., "Breast Tumor Cells with PI3K Mutation or HER2 Amplification Are Selectively Addicted to Akt Signaling" PLoS One 3(8):1-10 (2008).

Spoerke et al., "Phosphoinositide 3-Kinase (PI3K) Pathway Alterations Are Associated with Histologic Subtypes and Are Predictive of Sensitivity to PI3K Inhibitors in Lung Cancer Preclinical Models" Clin Cancer Res 18:6771-83 (2012).

Staben et al., "Cis-amide isosteric replacement in thienobenzoxepin inhibitors of PI3-kinase" Bioorg Med Chem Lett. 23(3):897-901 (2013).

Staben et al., "Discovery of thiazolobenzoxepin PI3-kinase inhibitors that spare the PI3-kinase β isoform" Biorg Med Chem Lett 23(9):2606-13 (May 1, 2013).

Staben et al., "Structure-based design of thienobenzoxepin inhibitors of PI3-kinase" Bioorg Med Chem Lett. 21:4054-8 (2011).

Vadas et al., "Structure basis for activation and inhibition of class I phosphoinositide 3-kinases" Science Signaling 4(195):1-12 (2011).

Vora Sadhna R. et al., "CDK 4/6 Inhibitors Scenitize PIK3CA Mutant Breast Cancer to PI3K Inhibitors" Cancer Cell (ISSN: 1535-6108), 26(1):136-149 (Jul. 14, 2014).

Wallin et al., "GDC-0941, a novel class I Selctive PI3K inhibitor, enhances the efficacy of docetaxel in human breast cancer models by increasing cell death in vitro and in vivo" Clin Cancer Res 18:3901-11 (2012).

Wallin et al., "Nuclear phospho-akt increased predicts synergy of PI3K inhibition and doxorubicin in breast cancer and ovarian cancer" Sci Transl Med 2(48):48ra66, (1-8) (2010).

Yang et al., "Strategically Timing Inhibition of Phosphatidylinositol 3-Kinase to Maximize Therapeutic Index in Estrogen Receptors Alpha-Positive, PIK3CA-Mutant Breast Cancer" Clin Cancer Res. 22(9):2250-60 (2016).

Zhou et al., "Flourine bonding—how does it work in protein-ligand interactions?" J Chem Inf Model. 49(10):2344-55 (Oct. 2009).

Search Report ROC (Taiwan) Application No. 106122915 dated Jul. 13, 2018.

* cited by examiner

BENZOXAZEPIN OXAZOLIDINONE COMPOUNDS AND METHODS OF USE

CROSS REFERENCE TO RELATED APPLICATIONS

This is a continuation of U.S. patent application Ser. No. 15/481,764, filed 7 Apr. 2017, now abandoned, which is a continuation application of U.S. Ser. No. 15/200,301, filed 1 Jul. 2016, now U.S. Pat. No. 9,650,393, issued 16 May 2017, and claims the benefit under 35 USC § 119(e) of U.S. Provisional Application Ser. No. 62/188,029 filed on 2 Jul. 2015, all of which are incorporated by reference in entireties.

FIELD OF THE INVENTION

The invention relates generally to benzoxazepin oxazolidinone compounds with activity against hyperproliferative disorders such as cancer. The invention also relates to methods of using the compounds for in vitro, in situ, and in vivo diagnosis or treatment of mammalian cells, or associated pathological conditions.

BACKGROUND OF THE INVENTION

Upregulation of the phosphoinositide-3 kinase (PI3K)/Akt signaling pathway is a common feature in most cancers (Yuan and Cantley (2008) Oncogene 27:5497-510). Genetic deviations in the pathway have been detected in many human cancers (Osaka et al (2004) Apoptosis 9:667-76) and act primarily to stimulate cell proliferation, migration and survival. Activation of the pathway occurs following activating point mutations or amplifications of the PIK3CA gene encoding the p110α (alpha) PI3K isoforms (Hennessy et al (2005) Nat. Rev. Drug Discov. 4:988-1004). Genetic deletion or loss of function mutations within the tumor suppressor PTEN, a phosphatase with opposing function to PI3K, also increases PI3K pathway signaling (Zhang and Yu (2010) Clin. Cancer Res. 16:4325-30. These aberrations lead to increased downstream signaling through kinases such as Akt and mTOR and increased activity of the PI3K pathway has been proposed as a hallmark of resistance to cancer treatment (Opel et al (2007) Cancer Res. 67:735-45; Razis et al (2011) Breast Cancer Res. Treat. 128:447-56).

Phosphatidylinositol 3-Kinase (PI3K) is a major signaling node for key survival and growth signals for lymphomas and is opposed by the activity of the phosphatase PTEN. The phosphoinositide 3-dependent kinase (PI3K) signaling pathway is the most dysregulated pathway in hormone receptor positive breast cancer (HR+BC). The PI3K pathway is also dysregulated in aggressive forms of lymphoma (Abubaker (2007) Leukemia 21:2368-2370). Eight percent of DLBCL (diffuse large B-cell lymphoma) cancers have PI3CA (phosphatidylinositol-3 kinase catalytic subunit alpha) missense mutations and 37% are PTEN negative by immunohistochemistry test.

Phosphatidylinositol is one of a number of phospholipids found in cell membranes, and which participate in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol Chem. 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60). Phosphoinositide 3-kinases (PI3K) are lipid kinases that phosphorylate lipids at the 3-hydroxyl residue of an inositol ring (Whitman et al (1988) Nature, 332:664). The 3-phosphorylated phospholipids (PIP3s) generated by PI3-kinases act as second messengers recruiting kinases with lipid binding domains (including plekstrin homology (PH) regions), such as Akt and PDK1, phosphoinositide-dependent kinase-1 (Vivanco et al (2002) Nature Rev. Cancer 2:489; Phillips et al (1998) Cancer 83:41).

The PI3 kinase family comprises at least 15 different enzymes sub-classified by structural homology and are divided into 3 classes based on sequence homology and the product formed by enzyme catalysis. The class I PI3 kinases are composed of 2 subunits: a 110 kd catalytic subunit and an 85 kd regulatory subunit. The regulatory subunits contain SH2 domains and bind to tyrosine residues phosphorylated by growth factor receptors with a tyrosine kinase activity or oncogene products, thereby inducing the PI3K activity of the p110 catalytic subunit which phosphorylates its lipid substrate. Class 1 PI3 kinases are involved in important signal transduction events downstream of cytokines, integrins, growth factors and immunoreceptors, which suggests that control of this pathway may lead to important therapeutic effects such as modulating cell proliferation and carcinogenesis. Class I PI3Ks can phosphorylate phosphatidylinositol (PI), phosphatidylinositol-4-phosphate, and phosphatidylinositol-4,5-biphosphate (PIP2) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidylinositol-4-phosphate. Class III PI3Ks can only phosphorylate PI. A key PI3-kinase isoform in cancer is the Class I PI3-kinase, p110α as indicated by recurrent oncogenic mutations in p110α (Samuels et al (2004) Science 304:554; U.S. Pat. No. 5,824,492; U.S. Pat. No. 5,846,824; U.S. Pat. No. 6,274,327). Other isoforms may be important in cancer and are also implicated in cardiovascular and immune-inflammatory disease (Workman P (2004) Biochem Soc Trans 32:393-396; Patel et al (2004) Proc. Am. Assoc. of Cancer Res. (Abstract LB-247) 95th Annual Meeting, March 27-31, Orlando, Fla., USA; Ahmadi K and Waterfield M D (2004) "Phosphoinositide 3-Kinase: Function and Mechanisms" Encyclopedia of Biological Chemistry (Lennarz W J, Lane M D eds) Elsevier/Academic Press), Oncogenic mutations of p110α (alpha) have been found at a significant frequency in colon, breast, brain, liver, ovarian, gastric, lung, and head and neck solid tumors. About 35-40% of hormone receptor positive (HR+) breast cancer tumors harbor a PIK3CA mutation. PTEN abnormalities are found in glioblastoma, melanoma, prostate, endometrial, ovarian, breast, lung, head and neck, hepatocellular, and thyroid cancers.

PI3 kinase (PI3K) is a heterodimer consisting of p85 and p110 subunits (Otsu et al (1991) Cell 65:91-104; Hiles et al (1992) Cell 70:419-29). Four distinct Class I PI3Ks have been identified, designated PI3K α (alpha), β (beta), δ (delta), and γ (gamma), each consisting of a distinct 110 kDa catalytic subunit and a regulatory subunit. Three of the catalytic subunits, i.e., p110 alpha, p110 beta and p110 delta, each interact with the same regulatory subunit, p85; whereas p110 gamma interacts with a distinct regulatory subunit, p101. The patterns of expression of each of these PI3Ks in human cells and tissues are distinct. In each of the PI3K alpha, beta, and delta subtypes, the p85 subunit acts to localize PI3 kinase to the plasma membrane by the interaction of its SH2 domain with phosphorylated tyrosine residues (present in an appropriate sequence context) in target proteins (Rameh et al (1995) Cell, 83:821-30; Volinia et al (1992) Oncogene, 7:789-93).

The PI3 kinase/Akt/PTEN pathway is an attractive target for cancer drug development since such agents would be expected to inhibit cellular proliferation, to repress signals from stromal cells that provide for survival and chemoresistance of cancer cells, to reverse the repression of apoptosis and surmount intrinsic resistance of cancer cells to cytotoxic agents. PI3K is activated through receptor tyrosine kinase signaling as well as activating mutations in the p110 catalytic subunit of PI3K, loss of the tumor suppressor PTEN, or through rare activating mutations in AKT.

Taselisib (GDC-0032, Roche RG7604, CAS Reg. No. 1282512-48-4, Genentech Inc.), named as 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide, has potent PI3K activity (Ndubaku, C. O. et al (2013) J. Med. Chem. 56:4597-4610; WO 2011/036280; U.S. Pat. No. 8,242,104; U.S. Pat. No. 8,343,955) and is being studied in patients with locally advanced or metastatic solid tumors. Taselisib (GDC-0032) is a beta-isoform sparing inhibitor of the PI3K catalytic subunit, 31× more selective for the alpha subunit, compared to beta. Taselisib displays greater selectivity for mutant PI3Kα isoforms than wild-type PI3Kα (Olivero A G et al, AACR 2013. Abstract DDT02-01). Taselisib is currently being developed as a treatment for patients with oestrogen receptor (ER)-positive, HER2-negative metastatic breast cancer (mBC) and non-small cell lung cancer (NSCLC). In the phase Ia study with single agent taselisib, partial responses (PRs) were observed in 6/34 enrolled to patients. All 6 responses were observed in patients with PIK3CA mutant tumors (Juric D. et al. AACR 2013), indicating the need to determine PIK3CA mutation status from patients treated with taselisib.

Recent clinical data with PI3K inhibitors has implicated PI3K delta activity as a source of gastrointestinal toxicities (Akinleye et al Phosphatidylinositol 3-kinase (PI3K) inhibitors as cancer therapeutics" Journal of Hematology & Oncology 2013, 6:88-104; C. Saura et al "Phase Ib Study of the PI3K Inhibitor Taselisib (GDC-0032) in Combination with Letrozole in Patients with Hormone Receptor-Positive Advanced Breast Cancer" San Antonio Breast Cancer Symposium—Dec. 12, 2014, PD5-2; Lopez et al "Taselisib, a selective inhibitor of PIK3CA, is highly effective on PIK3CA-mutated and HER2/neu amplified uterine serous carcinoma in vitro and in vivo" (2014) Gynecologic Oncology).

Idelalisib (GS-1101, CAL-101, ZYDELIG®, Gilead Sciences Inc., CAS Reg. No. 870281-82-6, 5-fluoro-3-phenyl-2-[(1S)-1-(7H-purin-6-ylamino)propyl]-4(3H)-quinazolinone) is a selective PI3Kδ (delta) inhibitor and approved for the treatment of chronic lymphoid leukemia, CLL (Somoza, J. R. et al (2015) J. Biol. Chem. 290:8439-8446; U.S. Pat. No. 6,800,620; U.S. Pat. No. 6,949,535; U.S. Pat. No. 8,138,195; U.S. Pat. No. 8,492,389; U.S. Pat. No. 8,637,533; U.S. Pat. No. 8,865,730; U.S. Pat. No. 8,980,901; RE44599; RE44638). Diarrhea and colitis are among the most common adverse events reported after idelalisib treatment (Brown et al "Idelalisib, an inhibitor of phosphatidylinositol 3-kinase p110d, for relapsed/refractory chronic lymphocytic leukemia" (2014) Blood 123(22):3390-3397; Zydelig® Prescribing Information 2014; Zydelig®) REMS Fact Sheet). The significant GI toxicities observed after treatment with idelalisib are consistent with the hypothesis that inhibition of PI3Kδ (delta) is a source of gastrointestinal toxicities. Additional serious side effects were seen in clinical trials of idelalisib (Zydelig®) in combination with other therapies. Adverse events, including deaths have been tied to infections such as pneumonia. In March 2016, the EMA's Pharmacovigilance Risk Assessment Committee (PRAC) issued a provisional warning and a recommendation that patients receive antibiotic co-treatment and are routinely monitored for infection when taking Zydelig (idelalisib). In March 2016, the US Food and Drug Administration issued an alert that "six clinical trials exploring idelalisib (Zydelig®) in combination with other therapies have been halted due to reports of an increased rate of adverse events, including death".

There is a need for additional modulators of PI3Kα that are useful for treating cancers, particularly an inhibitor of PI3Kα that is selective for mutant PI3Kα expressing tumors relative to non-mutant PI3Kα expressing cells. There is especially a need for such an agent that selectively inhibits the PI3Kα isoform relative to the PI3Kβ, PI3Kδ, and PI3Kγ isoforms, which may be expected to result in an enhanced therapeutic window.

SUMMARY OF THE INVENTION

The invention relates generally to benzoxazepin oxazolidinone compounds with selective activity in modulating mutant forms of the PI3Kα (alpha) isoform, and having the Formula I structure:

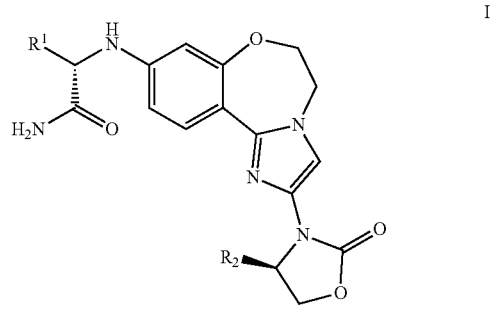

and stereoisomers, geometric isomers, tautomers, and pharmaceutically acceptable salts thereof. The various substituents are defined herein.

Another aspect of the invention is a pharmaceutical composition comprising a benzoxazepin oxazolidinone compound of Formula I, and a pharmaceutically acceptable carrier, glidant, diluent, or excipient.

Another aspect of the invention is a method of treating cancer in a patient having cancer comprising administering to said patient a therapeutically effective amount of a benzoxazepin oxazolidinone compound of Formula I.

Another aspect of the invention is a kit for the therapeutic treatment of breast cancer, comprising:

a) a benzoxazepin oxazolidinone compound of Formula I; and b) instructions for use in the therapeutic treatment of breast cancer

DETAILED DESCRIPTION OF EXEMPLARY EMBODIMENTS

Figure 1A:
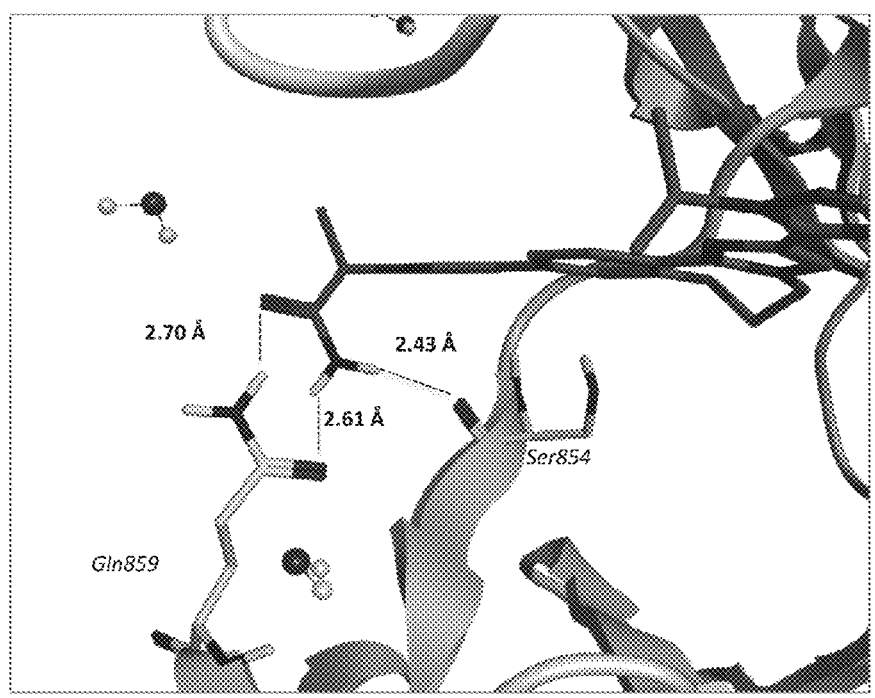
FIG. 1A shows the x-ray co-crystal structures of PI3Kα with taselisib (GDC-0032).

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. The nomenclature used in this Application is based on IUPAC systematic nomenclature, unless indicated otherwise.

DEFINITIONS

When indicating the number of substituents, the term "one or more" refers to the range from one substituent to the highest possible number of substitution, i.e. replacement of one hydrogen up to replacement of all hydrogens by substituents. The term "substituent" denotes an atom or a group of atoms replacing a hydrogen atom on the parent molecule. The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH($CH_3$)$_2$), 1-butyl (n-Bu, n-butyl, —$CH_2CH_2CH_2CH_3$), 2-methyl-1-propyl (i-Bu, i-butyl, —$CH_2$CH($CH_3$)$_2$), 2-butyl (s-Bu, s-butyl, —CH($CH_3$)$CH_2CH_3$), 2-methyl-2-propyl (t-Bu, t-butyl, —C($CH_3$)$_3$), 1-pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2CH_2CH_3$), 3-methyl-2-butyl (—CH($CH_3$)CH($CH_3$)$_2$), 3-methyl-1-butyl (—$CH_2CH_2$CH($CH_3$)$_2$), 2-methyl-1-butyl (—$CH_2$CH($CH_3$)$CH_2CH_3$), 1-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2CH_2CH_2CH_3$), 3-methyl-2-pentyl (—CH($CH_3$)CH($CH_3$)$CH_2CH_3$), 4-methyl-2-pentyl (—CH($CH_3$)$CH_2$CH($CH_3$)$_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2$CH($CH_3$)$_2$), 3,3-dimethyl-2-butyl (—CH($CH_3$)C($CH_3$)$_3$), 1-heptyl, 1-octyl, and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6.6] system, and bicyclic carbocycles having 9 or 10 ring atoms can be arranged as a bicyclo [5,6] or [6,6] system, or as bridged systems such as bicyclo[2.2.1]heptane, bicyclo [2.2.2]octane and bicyclo[3.2.2]nonane. Spiro carbocyclyl moieties are also included within the scope of this definition. Examples of spiro carbocyclyl moieties include [2.2]pentanyl, [2.3]hexanyl, and [2.4]heptanyl. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like.

Aryl groups are optionally substituted independently with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyclo[3.1.0]hexanyl, 3-azabicyclo[4.1.0]heptanyl, azabicyclo[2.2.2]hexanyl, 3H-indolyl quinolizinyl and N-pyridyl ureas. Spiro heterocyclyl moieties are also included within the scope of this definition. Examples of spiro heterocyclyl moieties include azaspiro[2.5]octanyl and azaspiro[2.4]heptanyl. Examples of a heterocyclic group wherein 2 ring atoms are substituted with oxo (=O) moieties are pyrimidinonyl and 1,1-dioxo-thiomorpholinyl.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The terms "treat" and "treatment" refer to therapeutic treatment, wherein the object is to slow down (lessen) an undesired physiological change or disorder, such as the development or spread of arthritis or cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those with the condition or disorder.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

"Hematological malignancies" (British spelling "Haematological" malignancies) are the types of cancer that affect blood, bone marrow, and lymph nodes. As the three are intimately connected through the immune system, a disease affecting one of the three will often affect the others as well: although lymphoma is a disease of the lymph nodes, it often spreads to the bone marrow, affecting the blood. Hematological malignancies are malignant neoplasms ("cancer"), and they are generally treated by specialists in hematology and/or oncology. In some centers "Hematology/oncology" is a single subspecialty of internal medicine while in others they are considered separate divisions (there are also surgical and radiation oncologists). Not all hematological disorders are malignant ("cancerous"); these other blood conditions may also be managed by a hematologist. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin. Leukemias include Acute lymphoblastic leukemia (ALL), Acute myelogenous leukemia (AML), Chronic lymphocytic leukemia (CLL). Chronic myelogenous leukemia (CML), Acute monocytic leukemia (AMOL) and small lymphocytic lymphoma (SLL). Lymphomas include Hodgkin's lymphomas (all four subtypes) and Non-Hodgkin's lymphomas (NHL, all subtypes).

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: ibrutinib (IMBRUVICA®, APCI-32765, Pharmacyclics Inc./Janssen Biotech Inc.; CAS Reg. No. 936563-96-1, U.S. Pat. No. 7,514,444), idelalisib (formerly CAL-101, GS 1101, GS-1101, Gilead Sciences Inc.; CAS Reg. No. 1146702-54-6), erlotinib (TARCEVA®, Genentech/OSI Pharm.), docetaxel (TAXOTERE, Sanofi-Aventis), 5-FU (fluorouracil, 5-fluorouracil, CAS Reg. No. 51-21-8), gemcitabine (GEMZAR®, Lilly), PD-0325901 (CAS No. 391210-10-9, Pfizer), cisplatin (Platinol®, (SP-4-2)-diamminedichloroplatinum(II), cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7,9-triene-9-carboxamide, CAS No. 85622-93-1, TEMODAR), TEMODALX, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®, CAS No. 23214-92-8), Akti-1/2, HPPD, and rapamycin.

Chemotherapeutic agents include inhibitors of B-cell receptor targets such as BTK, Bcl-2 and JAK inhibitors.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafamib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifamib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chlorambucil, AG1478, AG1571 (SU 5271; Sugen), temsirolimus (TORISEL®, Wyeth), pazopanib (GlaxoSmithKline), canfosfamide (TELCYTAX®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; mavtansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK, polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylomithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate) and selective estrogen receptor modulators (SERDs) such as fulvestrant (FASLODEX®, Astra Zeneca); (ii) aromatase inhibitors that inhibit the enzyme aromatase, which regulates estrogen production in the adrenal glands, such as, for example, 4(5)-imidazoles, aminoglutethimide. MEGASE® (megestrol acetate), AROMASIN (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors, such as cobimetinib (WO 2007/044515); (v) lipid kinase inhibitors, such as taselisib (GDC-0032, Genentech Inc.); (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN, Genentech/Biogen Idec), pertuzumab (PERJETA™, 2C4, Genentech), trastuzumab (HERCEPTIN®, Genentech), trastuzumab emtansine (KADCYLA®, Genentech Inc.), and tositumomab (BEXXAR, Corixia).

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a Formula I compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms. i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative, and depicted in Table 1 structures for illustrative purposes, while stereochemistry is definitively established, such as from x-ray crystallographic data.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "pharmaceutically acceptable salts" denotes salts which are not biologically or otherwise undesirable. Pharmaceutically acceptable salts include both acid and base addition salts. The phrase "pharmaceutically acceptable" indicates that the substance or composition must be compatible chemically and/or toxicologically, with the other ingredients comprising a formulation, and/or the mammal being treated therewith.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, aryl-aliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid mandelic acid, embonic acid, phenylacetic acid, methanesulfonic acid "mesylate", ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, and polyamine resins A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The term "$EC_{50}$" is the half maximal effective concentration" and denotes the plasma concentration of a particular compound required for obtaining 50% of the maximum of a particular effect in vivo.

The term "Ki" is the inhibition constant and denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (–log Ki), in which higher values indicate exponentially greater potency.

The term "$IC_{50}$" is the half maximal inhibitory concentration and denotes the concentration of a particular compound required for obtaining 50% inhibition of a biological process in vitro. $IC_{50}$ values can be converted logarithmically to $pIC_{50}$ values (–log $IC_{50}$), in which higher values indicate exponentially greater potency. The $IC_{50}$ value is not an absolute value but depends on experimental conditions e.g. concentrations employed, and can be converted to an absolute inhibition constant (Ki) using the Cheng-Prusoff equation (Biochem. Pharmacol. (1973) 22:3099). Other percent inhibition parameters, such as $IC_{70}$, $IC_{90}$, etc., may be calculated.

The terms "compound of this invention." and "compounds of the present invention" and "compounds of Formula I" include compounds of Formulas I and stereoisomers, geometric isomers, tautomers, solvates, metabolites, and pharmaceutically acceptable salts and prodrugs thereof.

Any formula or structure given herein, including Formula I compounds, is also intended to represent hydrates, solvates, and polymorphs of such compounds, and mixtures thereof.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, for example those into which radioactive isotopes such as 3H, 13C, and 14C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labeled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

Benzoxazepin Oxazolidinone Compounds

The present invention provides benzoxazepin oxazolidinone compounds of Formula I, and pharmaceutical formulations thereof, which are potentially useful in the treatment of cancer, having the structure:

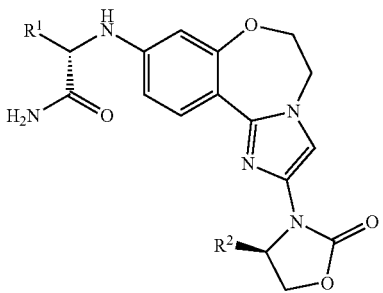

and stereoisomers, geometric isomers, tautomers, and pharmaceutically acceptable salts thereof, wherein:

$R^1$ is selected from —$CH_3$, —$CH_2CH_3$, cyclopropyl, and cyclobutyl;

$R^2$ is selected from —$CH_3$, —$CHF_2$, —$CH_2F$, and —$CF_3$.

Exemplary embodiments of Formula I compounds include wherein $R^1$ is —$CH_3$.

Exemplary embodiments of Formula I compounds include wherein $R^1$ is cyclopropyl.

Exemplary embodiments of Formula I compounds include wherein $R^2$ is —$CHF_2$.

Exemplary embodiments of Formula I compounds include the compounds in Table 1.

The Formula I compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. In some instances, the stereochemistry has not been determined or has been provisionally assigned.

In addition, the present invention embraces all diastereomers, including cis-trans (geometric) and conformational isomers. For example, if a Formula I compound incorporates a double bond or a fused ring, the cis- and trans-forms, as well as mixtures thereof, are embraced within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Biological Evaluation

The relative efficacies of Formula I compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$". Determination of $IC_{50}$ values can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

Exemplary Formula I compounds in Table 1 were made, characterized, and tested for binding to various isoforms and mutant forms of PI3K according to the methods of this invention, and have the following structures, corresponding names (ChemBioDraw, Version 12.0.2, CambridgeSoft Corp., Cambridge Mass.), and biological activity. Where more than one name is associated with a Formula I compound or intermediate, the chemical structure shall define the compound.

TABLE 1

Formula I compounds

| No. | Structure | Name |
|---|---|---|
| 101 | 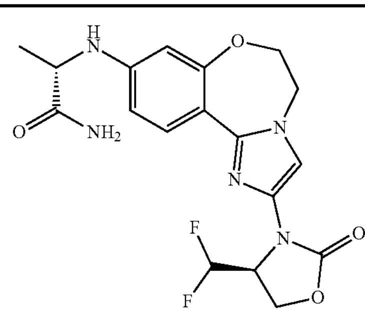 | (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide |

TABLE 1-continued

Formula I compounds

| No. | Structure | Name |
|---|---|---|
| 102 | 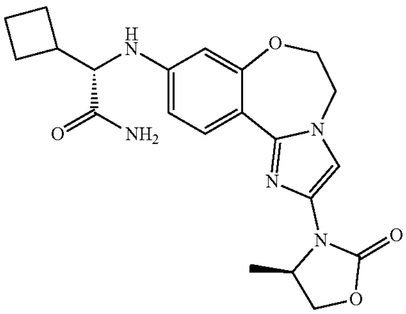 [SMILES: C[C@@H]1COC(=O)N1c1cn2c(n1)-c1ccc(N[C@H](C(N)=O)C3CCC3)cc1OCC2] | (S)-2-cyclobutyl-2-((2-((R)-4-methyl-2-oxooxazolidin-3-yl)-5,6-dihydrobenzo[f]imidazo[1,2-d][1,4]oxazepin-9-yl)amino)acetamide |
| 103 | 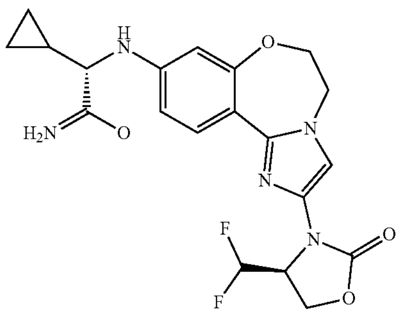 [SMILES: N=C(O)[C@@H](Nc1ccc2c(c1)OCCn1cc(N3C(=O)OC[C@H]3C(F)F)nc1-2)C1CC1] | (S)-2-cyclopropyl-2-((2-((S)-4-(difluoromethyl)-2-oxooxazolidin-3-yl)-5,6-dihydrobenzo[f]imidazo[1,2-d][1,4]oxazepin-9-yl)amino)acetamide |
| 104 | 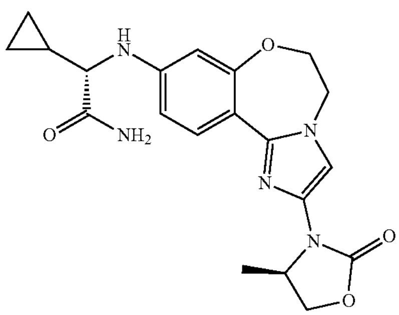 [SMILES: C[C@@H]1COC(=O)N1c1cn2c(n1)-c1ccc(N[C@H](C(N)=O)C3CC3)cc1OCC2] | (S)-2-cyclopropyl-2-((2-((R)-4-methyl-2-oxooxazolidin-3-yl)-5,6-dihydrobenzo[f]imidazo[1,2-d][1,4]oxazepin-9-yl)amino)acetamide |
| 105 | 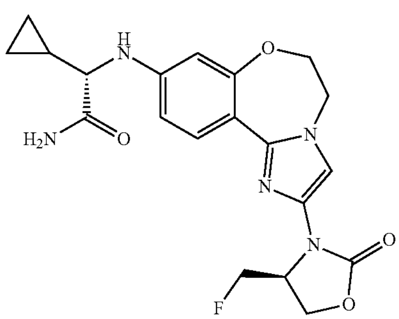 [SMILES: NC(=O)[C@@H](Nc1ccc2c(c1)OCCn1cc(N3C(=O)OC[C@H]3CF)nc1-2)C1CC1] | (S)-2-cyclopropyl-2-((2-((S)-4-(fluoromethyl)-2-oxooxazolidin-3-yl)-5,6-dihydrobenzo[f]imidazo[1,2-d][1,4]oxazepin-9-yl)amino)acetamide |
| 106 | 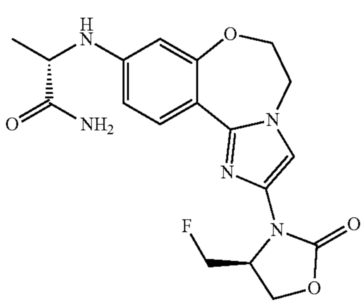 [SMILES: C[C@H](Nc1ccc2c(c1)OCCn1cc(N3C(=O)OC[C@H]3CF)nc1-2)C(N)=O] | (S)-2-((2-((S)-4-(fluoromethyl)-2-oxooxazolidin-3-yl)-5,6-dihydrobenzo[f]imidazo[1,2-d][1,4]oxazepin-9-yl)amino)propanamide |

TABLE 1-continued

Formula I compounds

| No. | Structure | Name |
|---|---|---|
| 107 | 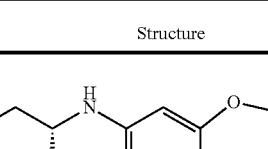 | (S)-2-((2-((S)-4-(difluoromethyl)-2-oxooxazolidin-3-yl)-5,6-dihydrobenzo[f]imidazo[1,2-d][1,4]oxazepin-9-yl)amino)butanamide |

Taselisib

The compound known as taselisib, GDC-0032, and Roche RG7604 (CAS Reg. No. 1282512-48-4, Genentech Inc.), has an IUPAC name: 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide, and the structure:

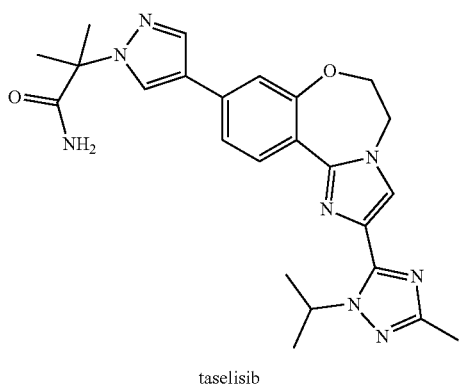 [SMILES: Cc1nc(-c2cn3c(n2)-c2ccc(-c4cnn(C(C)(C)C(N)=O)c4)cc2OCC3)n(C(C)C)n1]

taselisib including stereoisomers, geometric isomers, tautomers, and pharmaceutically acceptable salts thereof.

Taselesib can be prepared and characterized as described in WO 2011/036280, U.S. Pat. No. 8,242,104, and U.S. Pat. No. 8,343,955.

Pictilisib

The compound known as pictilisib, GDC-0941, Roche, RG-7321, and pictrelisib, (CAS Reg. No. 957054-30-7, Genentech Inc.,) is a potent multitargeted class I (pan) inhibitor of PI3K isoforms. GDC-0941 is currently in phase II clinical trials for the treatment of advanced solid tumors. GDC-0941 is named as 4-(2-(1H-indazol-4-yl)-6-((4-(methylsulfonyl)piperazin-1-yl)methyl)thieno[3,2-d]pyrimidin-4-yl)morpholine (U.S. Pat. No. 7,781,433; U.S. Pat. No. 7,750,002; Folkes et al (2008) Jour. of Med. Chem. 51(18): 5522-5532), and has the structure:

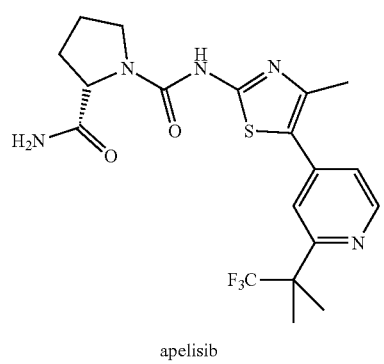

pictilisib including stereoisomers, geometric isomers, tautomers, and pharmaceutically acceptable salts thereof.

Alpelisib

The compound known as alpelisib (BYL719, Novartis, CAS #: 1217486-61-7) is an oral, selective inhibitor of the PI3K alpha isoform, and is in clinical trials for the potential treatment of a variety of tumor types, including a phase III study in combination with fulvestrant for second-line hormone receptor-positive. HER2-advanced metastatic breast cancer (Furet, P. et al (2013) Bioorg. Med. Chem. Lett. 23:3741-3748; U.S. Pat. No. 8,227,462; U.S. Pat. No. 8,476,268; U.S. Pat. No. 8,710,085). Alpelisib is named as (S)—N1-(4-methyl-5-(2-(1,1,1-trifluoro-2-methylpropan-2-yl)pyridin-4-yl)thiazol-2-yl)pyrrolidine-1,2-dicarboxamide) and has the structure:

apelisib

Biochemical Inhibition of PI3K Isoforms

The ability of a compound of the invention to act as an inhibitor of PI3Kα with selectivity over PI3Kβ, PI3Kδ, and PI3Kγ was determined using the methods of Example 901. The Ki values shown in Tables 2A and 2B represent the geometric mean of a minimum of three independent experiments unless otherwise noted.

Table 2A shows the biochemical inhibition of four PI3K isoforms by the Formula I compounds of Table 1. In addition, two clinically tested PI3K compounds, taselisib and pictilisib are included as comparators. The representative compounds of the invention exhibit strong activity against PI3Kα, and exhibit significantly enhanced selectivity relative to the other isoforms PI3Kβ, PI3Kδ, and PI3Kγ when compared to taselisib (GDC-0032) and pictilisib (GDC-0941). In particular, the selectivity ratios in the second from the right column of Table 2A show that each Formula I compounds 101-107 has a PI3K alpha to delta selectivity ratio far higher than taselisib or pictilisib. In fact, both taselisib and pictilisib have stronger activity against PI3K delta than against PI3K alpha. i.e. their selectivity ratios are less than 1. The selectivity ratios of Formula I compound 101-107 range from 301-fold to 634-fold.

Table 2B shows the biochemical inhibition of two PI3K isoforms, alpha and delta and the PI3K alpha to delta selectivity ratios for certain comparator compounds of U.S. Pat. No. 8,242,104, and a compound bearing a dimethyloxazolidin-2-one group from U.S. Pat. No. 8,263,633 (Compound 356, column 149). The comparator compounds shown here in Table 2B are examples from the broad genuses described in each of U.S. Pat. No. 8,242,104 and U.S. Pat. No. 8,263,633. Neither U.S. Pat. No. 8,242,104 nor U.S. Pat. No. 8,263,633 discloses a compound within the scope of the Formula I compounds of the invention. While the representative comparator examples of U.S. Pat. No. 8,242,104 as described in Table 2B demonstrate PI3Kα (alpha) vs. PI3Kδ (delta) selectivity ratios>1, the maximum observed selectivity ratio is 46.9-fold. Formula I compounds 101-107 therefore achieve significantly higher selectivity ratios than examples of U.S. Pat. No. 8,242,104. There is no guidance in either U.S. Pat. No. 8,242,104 or U.S. Pat. No. 8,263,633 to make the selection of structural elements of the Formula I compounds to achieve the property of high PI3K alpha selectivity versus PI3K delta. This unexpected property of greater than 300-fold PI3K alpha selectivity is conserved across the entire spectrum of the compounds exemplified in Table 1.

Current PI3K inhibitors in clinical trials, such as taselisib (WO 2011/036280; U.S. Pat. No. 8,242,104; U.S. Pat. No. 8,343,955), and other representative examples of U.S. Pat. No. 8,242,104 exhibit significant activity against the PI3Kδ (delta) isoform. This lack of selectivity vs. PI3Kδ (delta) is consistent with observed GI toxicity in the clinic for taselisib. There exists a need for inhibitors of PI3Kα (alpha) that contain the favorable characteristics representative of examples of U.S. Pat. No. 8,242,104 that are simultaneously lacking activity against PI3Kδ (delta). The current invention provides compounds that meet this activity and selectivity profile.

The unexpected property of PI3K alpha selectivity is advantageous to remove gastrointestinal toxicity observed in clinical PI3K inhibitor candidates. Recent clinical data with PI3K inhibitors has implicated PI3K delta activity as a source of gastrointestinal toxicities (Akinleye et al, "Phosphatidylinositol 3-kinase (PI3K) inhibitors as cancer therapeutics" Journal of Hematology & Oncology 2013, 6:88-104). See Table 2 of PI3K inhibitors in clinical trials, taselisib and pictilisib.

With significantly higher selectivity for PI3Kα (alpha) inhibition relative to PI3Kδ (delta) inhibition, Formula I compounds 101-107 would therefore be expected to achieve a greater margin between clinical activity driven by PI3Kα (alpha) inhibition relative to toxicities driven by PI3Kδ (delta) inhibition, as compared to the clinically tested taselisib and pictilisib or any of the examples of U.S. Pat. No. 8,242,104 or U.S. Pat. No. 8,263,633. Accordingly, Formula I compounds of the invention may be useful as therapeutic agents with a decreased toxicity profile relative to agents that exhibit greater inhibition of the normal functions of PI3Kβ, PI3Kδ, or PI3Kγ.

TABLE 2A

Biochemical inhibition of PI3K isoforms by Formula I compounds and comparator compounds taselisib and pictilisib

| Compound No. | PI3Kα Ki (nM) | PI3Kβ Ki (nM) | PI3Kδ Ki (nM) | PI3Kγ Ki (nM) | Selectivity for PI3Kα vs. PI3K-β | Selectivity for PI3Kα vs. PI3Kδ | Selectivity for PI3Kα vs. PI3Kγ |
|---|---|---|---|---|---|---|---|
| taselisib GDC-0032 | 0.090 | 53.0 | 0.079 | 1.43 | 591 | 0.9 | 16.0 |
| pictilisib GDC-0941 | 2.56 | 70.2 | 1.54 | 41.8 | 27.4 | 0.6 | 16.3 |
| 101 | 0.034 | 99.7 | 12.2 | 18.2 | 2944 | 361 | 537 |
| 102 | 0.949 | >1000 | 286 | 708 | >1054 | 301 | 746 |
| 103 | 0.060 | 335 | 37.7 | 49.0 | 5640 | 634 | 824 |
| 104 | 0.464 | 813 | 197 | 289 | 1750 | 425 | 622 |
| 105 | 0.051 | 341 | 30.3 | 36.4 | 6718 | 598 | 717 |
| 106 | 0.040 | 122 | 16.7 | 17.8 | 3050 | 416 | 444 |
| 107 | 0.048 | 132 | 17.5 | 23.7 | 2782 | 368 | 499 |

TABLE 2B

Biochemical inhibition of PI3K isoforms by comparator compounds

| No. (U.S. Pat. No. 8,242,104) | Structure | PI3Kα Ki (nM) | PI3Kδ Ki (nM) | Selectivity for PI3Kα vs. PI3Kδ |
|---|---|---|---|---|
| 196 taselisib GDC-0032 | 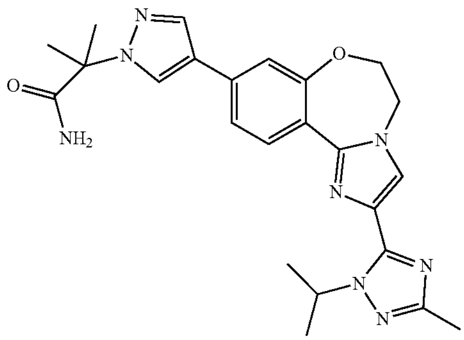 [SMILES: Cc1nc(-c2cn3c(n2)-c2ccc(-c4cnn(C(C)(C)C(N)=O)c4)cc2OCC3)n(C(C)C)n1] | 0.090 | 0.079 | 0.88 |
| 375 | 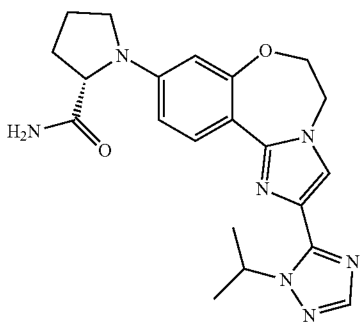 [SMILES: CC(C)n1ncnc1-c1cn2c(n1)-c1ccc(N3CCC[C@H]3C(N)=O)cc1OCC2] | 0.016 | 0.417 | 21.7 |
| 436 | 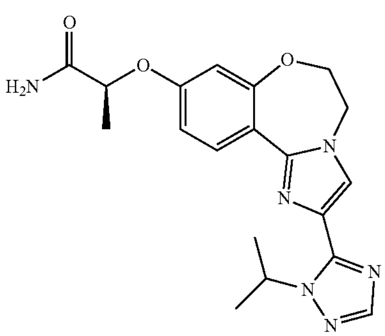 [SMILES: CC(C)n1ncnc1-c1cn2c(n1)-c1ccc(O[C@@H](C)C(N)=O)cc1OCC2] | 0.35 | 6.94 | 22.3 |
| 469 | 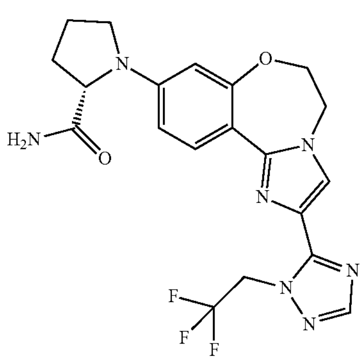 [SMILES: NC(=O)[C@@H]1CCCN1c1ccc2c(c1)OCCn1cc(-c3ncnn3CC(F)(F)F)nc1-2] | <0.02* | 0.39* | 19.3 |

TABLE 2B-continued

Biochemical inhibition of PI3K isoforms by comparator compounds

| No. (U.S. Pat. No. 8,242,104) | Structure | PI3Kα Ki (nM) | PI3Kδ Ki (nM) | Selectivity for PI3Kα vs. PI3Kδ |
|---|---|---|---|---|
| 486 | 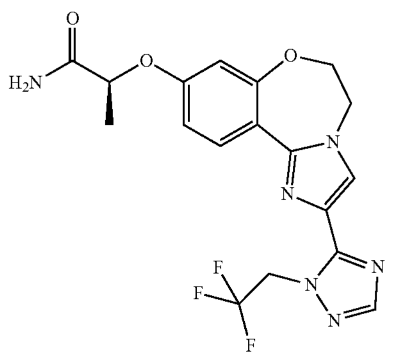 [SMILES: C[C@H](Oc1ccc2c(c1)OCCn1cc(-c3ncnn3CC(F)(F)F)nc1-2)C(N)=O] | 0.186 | 2.5 | 13.4 |
| 501 | 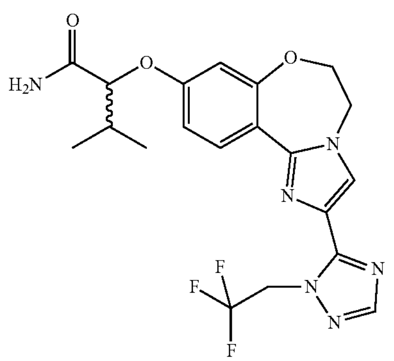 [SMILES: CC(C)C(Oc1ccc2c(c1)OCCn1cc(-c3ncnn3CC(F)(F)F)nc1-2)C(N)=O] | 3.56 | 21.8 | 6.1 |
| 529 | 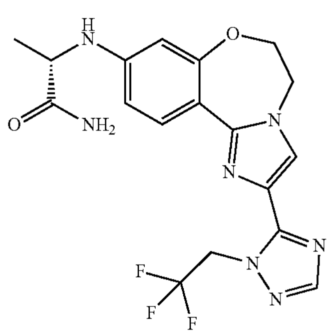 [SMILES: C[C@H](Nc1ccc2c(c1)OCCn1cc(-c3ncnn3CC(F)(F)F)nc1-2)C(N)=O] | 0.023 | 1.05 | 46.9 |
| 540 | 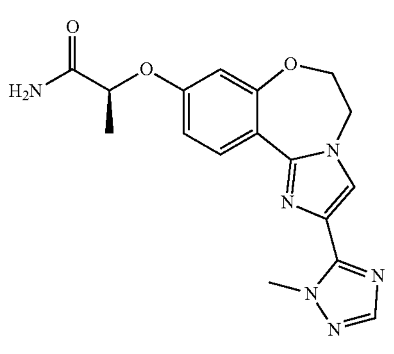 [SMILES: C[C@H](Oc1ccc2c(c1)OCCn1cc(-c3ncnn3C)nc1-2)C(N)=O] | 2.72 | 24.1 | 8.8 |

TABLE 2B-continued

Biochemical inhibition of PI3K isoforms by comparator compounds

| No. (U.S. Pat. No. 8,242,104) | Structure | PI3Kα Ki (nM) | PI3Kδ Ki (nM) | Selectivity for PI3Kα vs. PI3Kδ |
|---|---|---|---|---|
| 544 | 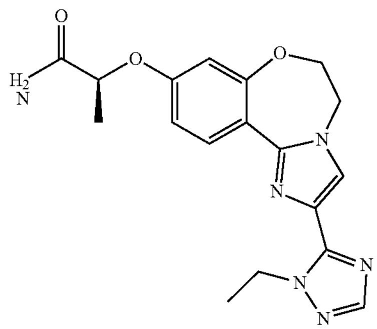 [SMILES: CCn1ncnc1-c1cn2c(n1)-c1ccc(O[C@@H](C)C(N)=O)cc1OCC2] | 0.437 | 11.3 | 25.8 |
| 549 (separated stereoisomer 1) | 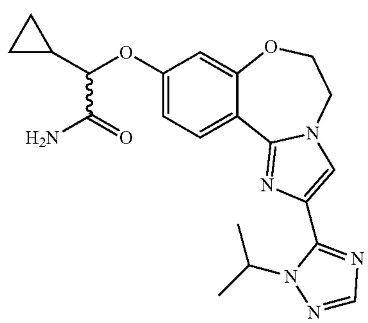 [SMILES: CC(C)n1ncnc1-c1cn2c(n1)-c1ccc(OC(C(N)=O)C3CC3)cc1OCC2] | 0.56 | 9.41 | 17.0 |
| 549 (separated stereoisomer 2) | 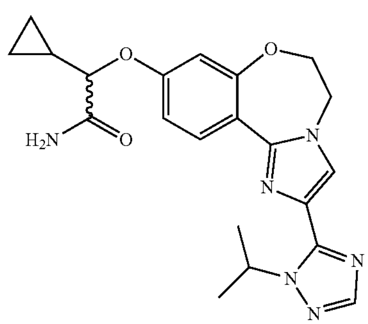 [SMILES: CC(C)n1ncnc1-c1cn2c(n1)-c1ccc(OC(C(N)=O)C3CC3)cc1OCC2] | 5.66 | 1.70 | 0.30 |
| 550 | 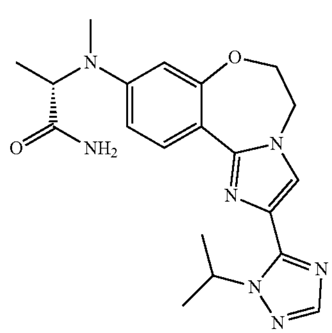 [SMILES: CC(C)n1ncnc1-c1cn2c(n1)-c1ccc(N(C)[C@@H](C)C(N)=O)cc1OCC2] | 0.107 | 1.96 | 19.4 |

TABLE 2B-continued

Biochemical inhibition of PI3K isoforms by comparator compounds

| No. (U.S. Pat. No. 8,242,104) | Structure | PI3Kα Ki (nM) | PI3Kδ Ki (nM) | Selectivity for PI3Kα vs. PI3Kδ |
|---|---|---|---|---|
| 356 (U.S. Pat. No. 8,263,633) | 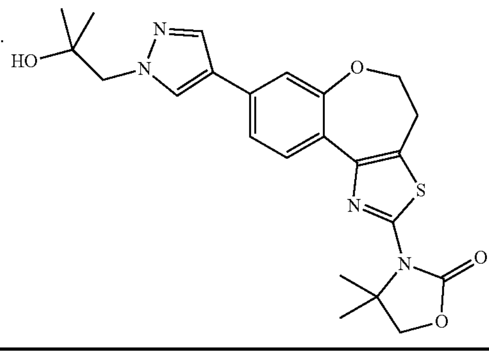 | 0.967 | 0.92 | 0.95 |

*Ki value represents the average of two experiments,
**Ki value represents a single experiment Interactions of Compounds with PI3K A rational basis for PI3Kα selectivity by the Formula I compounds may reside in certain binding interactions.

The ability of a compound of the invention to interact specifically with PI3Kα was determined by solving the x-ray co-crystal structure of representative compounds with PI3Kα (alpha) using the methods of Example 908. Optimized structural design of PI3K inhibitors with selectivity for the PI3Kα isoform over other isoforms may include precise positioning and arrangement of atoms and functional groups to interact with isoform-specific residues in the binding site. Particularly, substitution at the 9-position and at the 2-position of the 5,6-dihydrobenzo[f]imidazo[1,2-d][1,4]oxazepine ring system are found to have critical impacts on specific activity of compounds against PI3Kα.

FIGS. 1A-D show the x-ray co-crystal structures of taselisib (GDC-0032), reference compound 529 (U.S. Pat. No. 8,242,104) and two representative compounds of the invention with PI3Kα. As shown in FIG. 1A, taselisib (GDC-0032) contains a primary amide functional group that is positioned within close contact of both Gln859 and Ser854, appearing to offer the possibility of hydrogen-bonding interactions. The residue Gln859 is specific to the PI3Kα isoform, with a different residue occupying this position in the other isoforms (PI3Kβ=Asp, PI3Kδ=Asn, PI3Kγ=Lys). However, despite this close contact with a PI3Kα-specific residue, as measured in a biochemical assay GDC-0032 has equal activity against both isoforms PI3Kα and PI3Kδ, and only slightly reduced activity against the isoform PI3Kγ (see Table 2A).

Figure 1B:
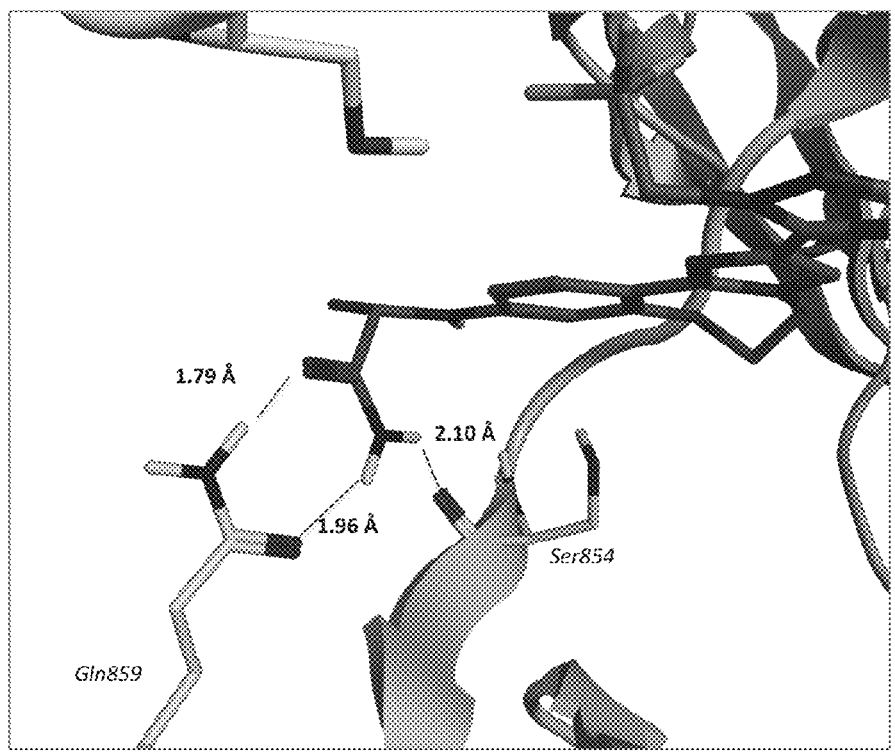
FIG. 1B shows the x-ray co-crystal structures of PI3Kα with Compound 529 of U.S. Pat. No. 8,242,104.

As shown in FIG. 1B, reference compound 529 (U.S. Pat. No. 8,242,104) contains a primary amide functional group in a similar position to that of taselisib. This functionality is within appropriate distance and of appropriate geometry of both Ser854 and Gln859 to make hydrogen-bonding interactions. The 46.9-fold selectivity ratio for PI3Kα relative to PI3Kδ (see Table 2B) may be rationalized in light of these interactions, and the knowledge that PI3Kδ does not contain a Gln residue at position 859 and therefore these interactions should be specific to PI3Kα.

Figure 1C:
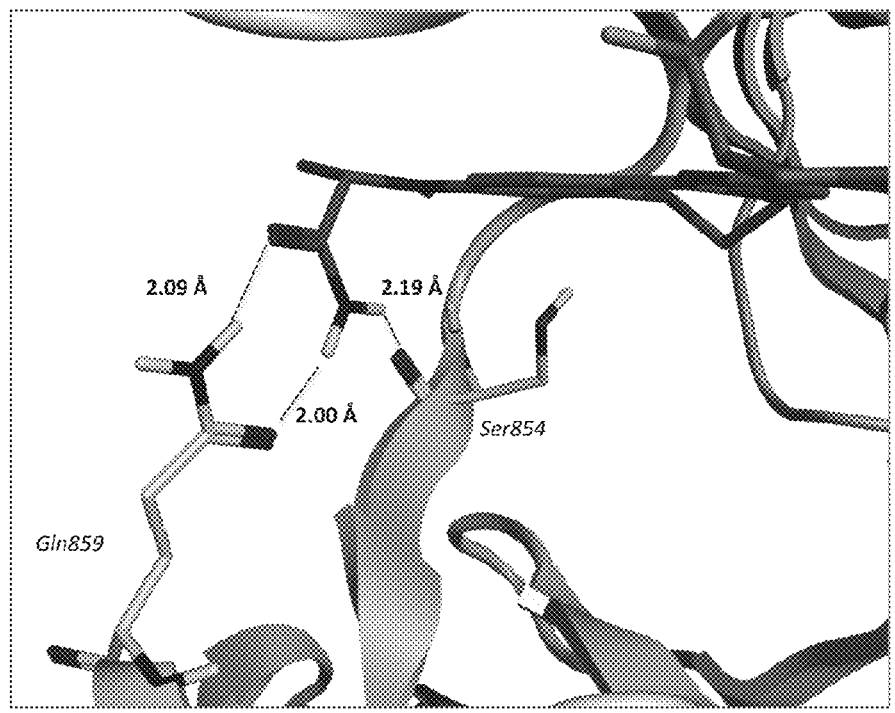
FIG. 1C shows the x-ray co-crystal structures of PI3Kα with Compound 101.
Figure 1D:
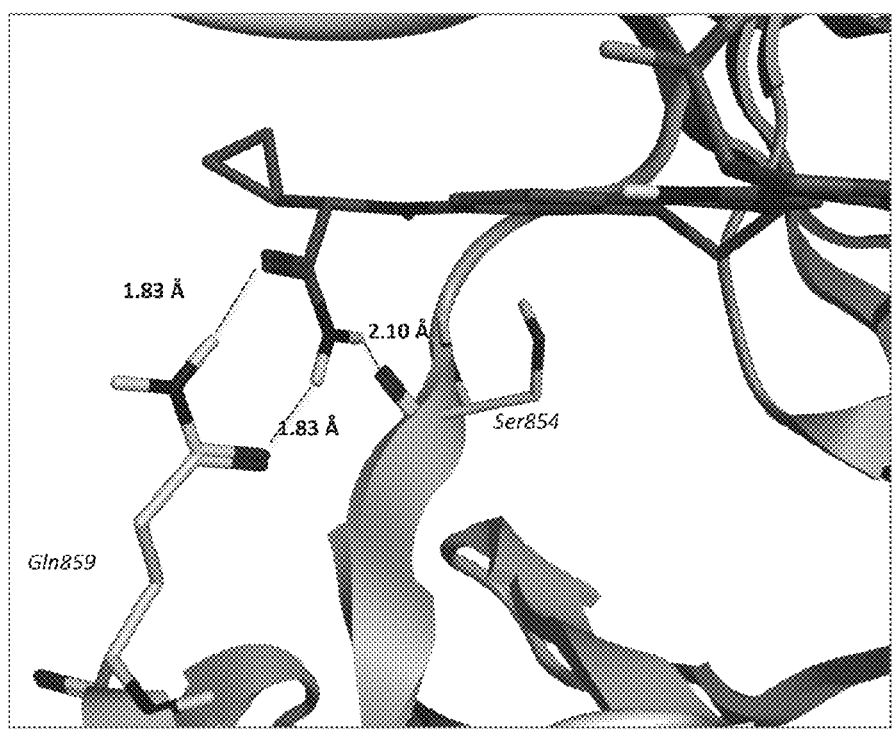
FIG. 1D shows the x-ray co-crystal structures of PI3Kα with Compound 103.

FIGS. 1C and 1D show that the primary amide of the (S)-2-aminopropanamide group of Compound 101 and the (S)-2-amino-2-cyclopropylacetamide group of Compound 103 each occupy a very similar place in the binding site to the primary amides of GDC-0032 and reference compound 529 (U.S. Pat. No. 8,242,104). This primary amide functionality in each representative of the invention is within appropriate distance and of appropriate geometry of both Ser854 and Gln859 to make ideal hydrogen bonding interactions. Despite the apparent similarities in functional group placement and orientation, the representative examples illustrated in FIGS. 1C and 1D, as well as other compounds of this invention with similar substituents and functionality, improve upon the interactions of the primary amide of both taselisib and reference compound 529 (U.S. Pat. No. 8,242,104) such that compounds of this invention are observed to have substantially increased selectivity for PI3Kα relative to PI3Kδ as measured in a biochemical assay. Compound 101 is 361-fold selective and Compound 103 is 634-fold selective, a substantial increase relative to reference compound 529 (U.S. Pat. No. 8,242,104) which is only 46.9-fold selective. In light of the similarity of the positioning of the primary amide functionality between taselisib and other compounds of U.S. Pat. No. 8,242,104 (as exemplified by reference compound 529), the increased selectivity for PI3Kα relative to PI3Kδ as demonstrated by compounds of this invention is an unexpected property. There is no guidance in U.S. Pat. No. 8,242,104 to make the selection of structural elements of the Formula I compounds to achieve the property of high (>300-fold) PI3Kα selectivity. The Formula I compounds of the invention improve upon the interactions of the primary amide of GDC-0032 such that compounds of this invention are observed to have substantially increased selectivity for PI3Kα relative to PI3Kδ as measured in a biochemical assay relative to comparator compounds (see Tables 2A and 2B).

Figure 2A:
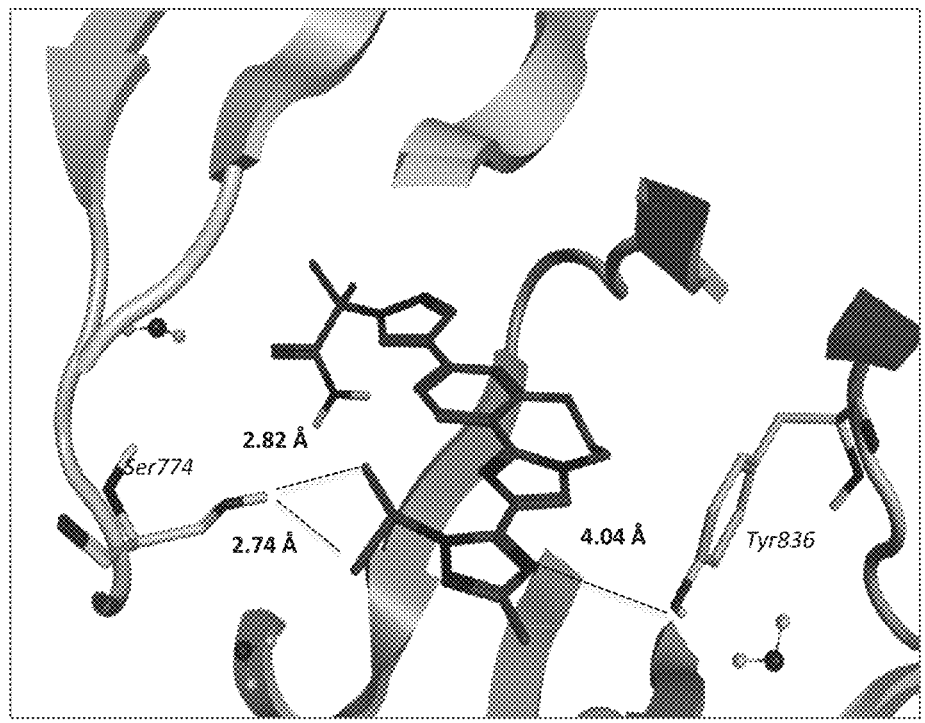
FIG. 2A shows the x-ray co-crystal structures of PI3Kα with taselisib (GDC-0032).
Figure 2B:
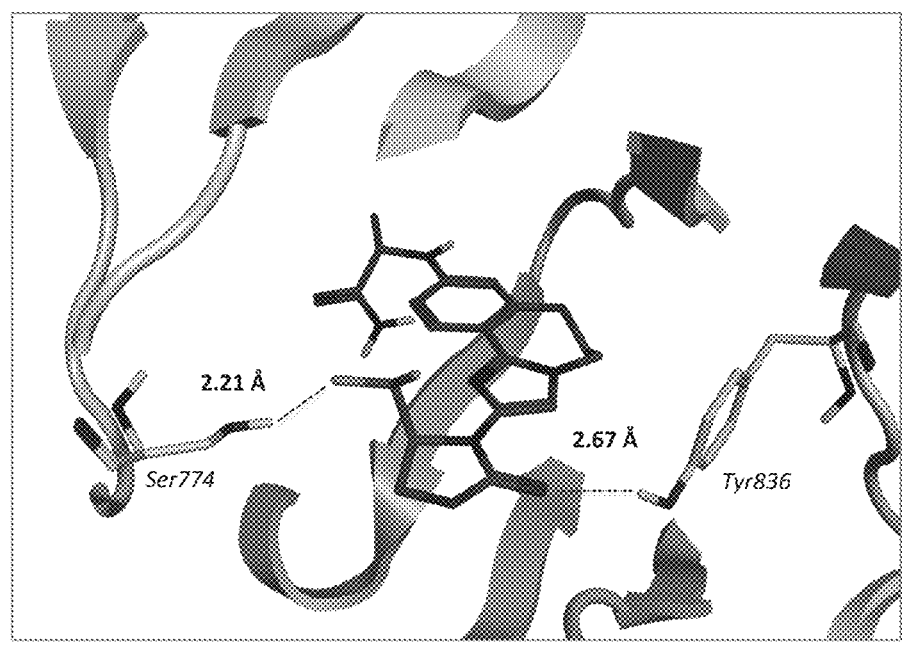
FIG. 2B shows the x-ray co-crystal structures of PI3Kα with Compound 101.

FIG. 2A shows an x-ray structure of taselisib bound in the PI3Kα (alpha) active site. The N2 atom of the triazole ring is not able to interact directly with either the side-chain of Tyr836 (distance of 4.04 Å) or Ser774 (distance of 2.74 and 2.82 Å, no complementary polarity between ligand and residue). FIG. 2B shows an x-ray structure of Compound 101 bound in the PI3Kα active site, and shows that the oxazolidinone ring is able to make multiple improved interactions with the protein relative to the triazole ring. The carbonyl functionality is close to the Tyr836 side chain (2.67

Å) and able to make a favorable polar interaction. A fluorine atom of the oxazolidinone substituent is in close contact (2.21 Å) with the hydroxyl group of Ser774 and is consistent with a polar interaction or non-classical hydrogen bond, a favorable interaction enabled by polarization of the carbon-fluorine bond (Böhm et. al, Fluorine in Medicinal Chemistry, (2004) ChemBioChem, 5:637-643; Zhou et. al, "Fluorine Bonding—How Does it Work In Protein-Ligand Interactions", (2009) J. Chem. Inf. Model., 49:2344-2355).

All compounds of the invention contain an oxazolidinone ring and are able to make the improved interaction with Tyr836 of PI3Kα (alpha). Some examples of the invention also contain a fluorinated substituent on the oxazolidinone ring and are able to make the improved interaction with Ser774 of PI3Kα. Both of these binding interactions may contribute to the enhanced selectivity for PI3Kα observed for examples of the invention relative to examples of U.S. Pat. No. 8,242,104. As shown in Tables 2A and 2B, compounds which contain the oxazolidinone ring have higher isoform selectivity than comparable compounds which contain the triazole ring. The residues Ser774 and Tyr836 are not unique to the PI3Kα isoform, PI3Kδ contains these same residues at the same positions, and the enhanced isoform selectivity of the oxazolidinone inhibitors is not predicted by these crystal structures. Subtle differences in the positioning and orientation of the same residue identity between different isoforms may result from subtle changes in secondary and tertiary protein structure. These differences are difficult to predict and interpret even in the face of x-ray crystal structures of both protein isoforms. The surprising and unexpected properties of improved molecular interactions and enhanced isoform selectivity of oxazolidinone inhibitors is conserved across the entire spectrum of the compounds exemplified in Table 1.

The oxazolidinone is structurally differentiated from the triazole in that the oxazolidinone has a carbonyl, is more polar, and does not have aromatic character. The triazole does not have a carbonyl group, is less polar, and has aromatic character.

The oxazolidinone ring provides a further benefit relative to the triazole ring in terms of increased sp3 character and reduced aromatic ring count. It is generally accepted in the literature that an increased number of aromatic rings is correlated with an increased risk of promiscuous binding. By contrast, an increase in the fraction of sp3 carbons (# sp3 carbons/# total carbons) is correlated with improved physicochemical properties and decreased promiscuous binding, decreasing the risk of off-target toxicology. These concepts are described in the references Lovering et. al, "Escape From Flatland", (2009) J. Med. Chem., 52:6752-6756 and Ritchie and Macdonald, "Physicochemical Descriptors of Aromatic Character and Their Use in Drug Discovery", (2014) J. Med. Chem., 57:7206-7215. The replacement of the triazole aromatic ring as exemplified by representatives of U.S. Pat. No. 8,242,104 with a saturated heterocyclic ring, the oxazolidinone contained within every example of the invention, represents a favorable decrease in the risk of off-target toxicology. The entirety of exemplified compounds in U.S. Pat. No. 8,242,104 are overwhelmingly populated by compounds with aromatic rings at this position, 4 examples of a carboxamide functional group replacing the aromatic ring, and no examples of saturated cyclic or heterocyclic systems. Due to the significantly different binding interactions and steric requirements of aromatic and saturated heterocycles, they are typically not interchangeable. With no examples of saturated heterocyclic systems at the 2-position of the 5,6-dihydrobenzo[f]imidazo[1,2-d][1,4]oxazepine ring, U.S. Pat. No. 8,242,104 provides no guidance as to a method for replacing the aromatic ring with a saturated heterocycle while retaining activity against PI3Kα.

Accordingly, compounds of the invention contain optimized substituents and functionality at both the 5,6-dihydrobenzo[f]imidazo[1,2-d][1,4]oxazepine 9-position and 2-position. These optimized compounds provide a significant and heretofore unknown benefit with respect to improved molecular interactions and increased selective activity against PI3Kα, with reduced activity against PI3Kδ. The compounds of the invention may be useful as therapeutic agents with an enhanced therapeutic window relative to related agents such as taselisib (GDC-0032).

Selective Inhibition of Mutant PI3Kα (Alpha)

The ability of a compound of the invention to act preferentially against cells containing mutant PI3Kα was determined by measuring inhibition of the PI3K pathway in SW48 isogenic cell lines: PI3Kα wild-type (parental), helical domain mutant E545K, and kinase domain mutant H1047R, as described in the methods of Example 902.

Statistical Analysis: EC50 values represent the geometric mean of a minimum of 4 independent experiments unless otherwise noted. All statistics were performed using KaleidaGraph Software (version 4.1.3). A Student t-Test was performed using unpaired data with equal variance to compare activity against mutant cells and wild-type cells. P<0.05 is considered to be significant.

Table 3A shows the inhibition of P-PRAS40 in SW48 isogenic cells by the Formula I compounds of Table 1. These compounds all display increased activity against the mutant PI3Kα cells relative to the wild-type PI3Kα cells. Compounds of the invention show similar activity as taselisib in SW48 mutant PI3Kα cells, with equal or greater selectivity than taselisib relative to activity in the wild-type PI3Kα cells (see Table 3B).

Table 3B shows the inhibition of P-PRAS40 in SW48 isogenic cells by certain comparator compounds of U.S. Pat. No. 8,242,104, a compound bearing a dimethyloxazolidin-2-one group from U.S. Pat. No. 8,263,633 (Compound 356, column 149), and pictilisib. The comparator compounds shown here in Table 3B are examples from the broad genuses described in each of U.S. Pat. No. 8,242,104 and U.S. Pat. No. 8,263,633. Neither U.S. Pat. No. 8,242,104 nor U.S. Pat. No. 8,263,633 disclose a compound within the scope of the Formula I compounds of the invention. The comparator compounds contain examples that do not have significantly increased activity for the mutant PI3Kα cells relative to the wild-type PI3Kα cells (see comparator compounds 436 and 549, p>0.05). These compounds are very structurally similar to comparator compounds that do exhibit significantly increased activity for the mutant PI3Kα cells relative to the wild-type PI3Kα cell (see comparator compound 529). There is no common structural element within the comparator compounds that provides guidance towards selective inhibition of mutant PI3Kα (alpha) cells. More broadly, there is no guidance in either U.S. Pat. No. 8,242,104 or U.S. Pat. No. 8,263,633 to make the selection of structural elements of the Formula I compounds to achieve increased or equivalent activity against the mutant PI3Kα cells relative to the wild-type PI3Kα cells. This unexpected property is conserved across the entire spectrum of the compounds exemplified in Table 1.

TABLE 3A

Inhibition of P-PRAS40 in SW48 isogenic cells by Formula I compounds

| No. | P-PRAS40 SW48 (E545K) EC50 (µM) | P-PRAS40 SW48 (H1047R) EC50 (µM) | P-PRAS40 SW48 (parental) EC50 (µM) | Fold Selectivity for SW48 (E545K) vs. SW48 (parental) | Fold Selectivity for SW48 (H1047R) vs. SW48 (parental) |
|---|---|---|---|---|---|
| 101 | 0.0027 | 0.0030 | 0.0063 | 2.4 (p < 0.001) | 2.1 (p = 0.002) |
| 102 | 0.0335 | 0.0358 | 0.0849 | 2.5 (p = 0.002) | 2.4 (p = 0.001) |
| 103 | 0.0041 | 0.0038 | 0.0101 | 2.5 (p < 0.001) | 2.6 (p < 0.001) |
| 104 | 0.0200 | 0.0228 | 0.0618 | 3.1 (p = 0.007) | 2.7 (p = 0.009) |
| 105 | 0.0042 | 0.0048 | 0.0125 | 3.0 (p = 0.007) | 2.6 (p = 0.007) |
| 106 | 0.0045 | 0.0044 | 0.0115 | 2.5 (p = 0.003) | 2.6 (p = 0.001) |
| 107 | 0.0053 | 0.0052 | 0.0108 | 2.0 (p = 0.003) | 2.1 (p = 0.003) |

TABLE 3B

Inhibition of P-PRAS40 in SW48 isogenic cells by comparator compounds

| Compound or No. (U.S. Pat. No. 8,242,104) | P-PRAS40 SW48 (E545K) EC50 (µM) | P-PRAS40 SW48 (H1047R) EC50 (µM) | P-PRAS40 SW48 (parental) EC50 (µM) | Fold Selectivity for SW48 (E545K) vs. SW48 (parental) | Fold Selectivity for SW48 (H1047R) vs. SW48 (parental) |
|---|---|---|---|---|---|
| 196 taselisib GDC-0032 | 0.0034 | 0.0040 | 0.0079 | 2.3 (p < 0.001) | 2.0 (p < 0.001) |
| pictilisib GDC-0941 | 0.0284 | 0.0321 | 0.0315 | 1.1 (p = 0.7) | 1.0 (p = 0.9) |
| 436 GDC-0326 | 0.0095 | 0.0092 | 0.0128 | 1.3 (p = 0.26) | 1.4 (p = 0.22) |
| 529 | 0.0008 | 0.0009 | 0.0016 | 2.2 (p < 0.001) | 2.0 (p = 0.002) |
| 549 (separated stereoisomer 1) | 0.0105* | 0.0147* | 0.0119* | 1.1 | 0.8 |

*EC50 represents a single experiment

Antiproliferative Activity in PI3K Mutant Tumor Cells

The ability of a compound of the invention to act on PI3K mutant tumor cells was determined by measuring the cell viability EC50 in HCC1954 cells (PI3Kα mutant H1047R) and MCF7 cells (PI3Kα mutant E545K) using the methods of Example 903. Table 4 shows that representative Formula I compounds 101 and 103 of the invention are able to inhibit the PI3K pathway and inhibit proliferation in HCC1954 cells and MCF7 cells with a similar level of potency as comparator compounds taselisib (compound 196, U.S. Pat. No. 8,242,104), pictilisib and compound 436 (U.S. Pat. No. 8,242,104).

TABLE 4

Anti-proliferative activity of PI3K compounds in mutant PI3K-alpha tumor cells

| Compound or No. | HCC1954 antiproliferative EC50 (µM) | MCF7 antiproliferative EC50 (µM) |
|---|---|---|
| Taselisib 196 (U.S. Pat. No. 8,242,104) GDC-0032 | 0.04 | 0.02 |
| pictilisib GDC-0941 | 0.75 | 0.12 |
| 436 (U.S. Pat. No. 8,242,104) | 0.35 | 0.09 |
| 101 | 0.06 | 0.03 |
| 103 | 0.07 | 0.03 |

In Vivo Efficacy

Tables 5-8 show data from in vivo tumor growth inhibition (TGI) studies with PI3K compounds. Tumor volume change was measured for 20 days or more in cohorts of immunocompromised mice bearing breast cancer xenografts, dosed daily by PO (oral) administration with vehicle and PI3K compounds (Example 904).

Table 5 shows that at maximum tolerated doses (MTD), GDC-0032 (taselisib), Compound 103 and Compound 101 are each more efficacious than alpelisib (BYL-719) in a PI3K mutant tumor model.

Table 6 shows that at doses lower than maximum tolerated dose, (i.e. 25 mg/kg), Compound 101 is more efficacious than GDC-0032 in a PI3K mutant tumor model. There is potential for greater therapeutic index (TI) with Compound 101 since maximum efficacy is reached before maximum tolerability.

Table 7 shows that at maximum tolerated doses, increased responses (PRs and CRs) are seen with Compound 101 compared to GDC-0032 in a PI3K mutant tumor model. Also, at maximum tolerated doses, GDC-0032 and BYL-719 are equally efficacious.

Table 8 shows that at maximum tolerated doses, GDC-0032 and Compound 101 are more efficacious than BYL-719, and Compound 101 is approximately as efficacious as GDC-0032 in a PI3K mutant tumor model.

TABLE 5

Comparison of maximum tolerated doses (MTD) of PI3K compounds in the HCC-1954x1 (ER−, PI3K$^{H1047R}$) breast xenograft model

| PI3K Compound | % TGI | PR | CR |
|---|---|---|---|
| BYL-719, 40 mg/kg QD, PO | 80 | 1 | 1 |
| GDC-0032, 15 mg/kg QD, PO | 118 | 4 | 0 |
| Compound 103, 100 mg/kg QD, PO | 120 | 4 | 3 |
| Compound 101, 50 mg/kg QD, PO | 129 | 10 | 0 |

TABLE 6

Dose ranging study of Compound 101 in the HCC-1954x1 (ER−, PI3K$^{H1047R}$) breast xenograft model

| PI3K Compound | % TGI | PR | CR |
|---|---|---|---|
| Compound 101, 0.5 mg/kg PO, QD | 19 | 0 | 0 |
| Compound 101, 1 mg/kg PO, QD | 60 | 2 | 0 |
| Compound 101, 2.5 mg/kg PO, QD | 68 | 1 | 0 |
| Compound 101, 5 mg/kg PO, QD | 84 | 0 | 0 |
| Compound 101, 25 mg/kg PO, QD | 140 | 7 | 0 |
| Compound 101, 50 mg/kg PO, QD | 149 | 6 | 0 |
| GDC-0032, 15 mg/kg PO, QD | 111 | 2 | 0 |

TABLE 7

Dose ranging study of Compound 101 in the
KPL-4 (ER-, PI3K$^{H1047R}$) breast xenograft model

| PI3K Compound | % TGI | PR | CR |
| --- | --- | --- | --- |
| Compound 101, 1 mg/kg PO, QD | 28 | 0 | 0 |
| Compound 101, 2.5 mg/kg PO, QD | 86 | 1 | 0 |
| Compound 101, 5 mg/kg PO, QD | 93 | 1 | 0 |
| Compound 101, 15 mg/kg PO, QD | 125 | 5 | 0 |
| Compound 101, 25 mg/kg PO, QD | 135 | 9 | 0 |
| Compound 101, 50 mg/kg PO, QD | 153 | 9 | 1 |
| GDC-0032 15 mg/kg PO, QD | 113 | 3 | 0 |

TABLE 8

Comparison of GDC-0032, Compound 101, and BYL-719 in
the HCI-003 (ER+, PI3K$^{H1047R}$) breast PDX xenograft model

| PI3K Compound | % TGI | PR | CR |
| --- | --- | --- | --- |
| BYL-719, 40 mg/kg PO, QD | 114 | 2 | 0 |
| GDC-0032, 15 mg/kg PO, QD | 162 | 6 | 1 |
| Compound 101, 50 mg/kg PO, QD | 175 | 5 | 2 |

Pathway Inhibition in Isolated B-Cells

The ability of a compound of the invention to inhibit the PI3K-pathway in B-cells was assessed by influence of the compounds on CD69 levels post agonistic a-IgM treatment using the methods of Example 906. The expression of CD69 in B-cells resultant from a-IgM treatment is believed to be driven by signaling through PI3Kδ (delta). Table 9 shows representative Formula 1 compounds are more selective inhibitors of pathway signaling in a PI3K-mutant line (SW48 (H1047R)) vs. B-cells (column 3) compared to taselisib, pictilisib, alpelisib, compound-436 (US U.S. Pat. No. 8,242,104) and idelalisib.

TABLE 9

Inhibition of CD69 expression in B-cells by select compounds.

| No. | B-cell a-IgM CD69 expression IC50 (µM), plasma-protein-binding corrected* | [B-cell a-IgM CD69 expression IC50, plasma-protein binding corrected*]/[p-PRAS40 SW48(H1047R) EC50] |
| --- | --- | --- |
| 101 | 0.047 | 16 |
| 103 | 0.076 | 20 |
| taselisib | 0.00031 | 0.077 |
| pictilisib | 0.006 | 0.19 |
| alpelisib | 0.048 | 0.79 |
| Compound 436 (U.S. Pat. No. 8,242,104) | 0.020 | 2.2 |
| idelalisib | 0.048 | <0.048 |

*CD69 expression IC50 measured in human whole-blood and corrected by multiplying by measured human $f_u$ from a plasma protein binding experiment.

Pathway Inhibition in PI3K Mutant and Wild-Type Tumor Cells

The ability of a compound of the invention to inhibit PI3K-pathway signaling in tumor cells was assessed by measuring p-PRAS40 levels in HCC1954 (PI3Kα mutant H1047R) and HDQ-P1 (PI3Kα wild-type) lines, using the methods of Example 907. Table 10 shows representative Formula 1 compounds 101, 103 and 105 are able to inhibit the PI3K pathway selectively in PI3Kα mutant (HCC1954, PI3Kα mutant H1047R) vs. PI3Kα wild-type tumor cells (HDQ-PI, PI3Kα wild-type). Compounds 101, 103 and 105 have greater mutant over wild-type selectivity than comparator compounds taselisib, pictilisib, alpelisib and compound-436 (U.S. Pat. No. 8,242,104).

TABLE 10

Inhibition of p-PRAS40 in HCC1954 and HDQ-P1 lines by select compounds.

| No. | P-PRAS40 HCC1954 MSD EC50 (µM) | P-PRAS40 HDQ-P1 MSD EC50 (µM) | Fold Selectivity for HCC1954 vs. HDQ-P1 |
| --- | --- | --- | --- |
| 101 | 0.019 | 0.084 | 4.4 |
| 103 | 0.028 | 0.155 | 5.5 |
| 105 | 0.027 | 0.179 | 6.6 |
| taselisib | 0.023 | 0.055 | 2.4 |
| pictilisib | 0.324 | 0.094 | 0.3 |
| alpelisib | 0.483 | 0.311 | 0.6 |
| Compound 436 (U.S. Pat. No. 8,242,104) | 0.089 | 0.122 | 1.4 | p110α Degradation in PI3K Mutant Tumor Cells

Figure 3A:
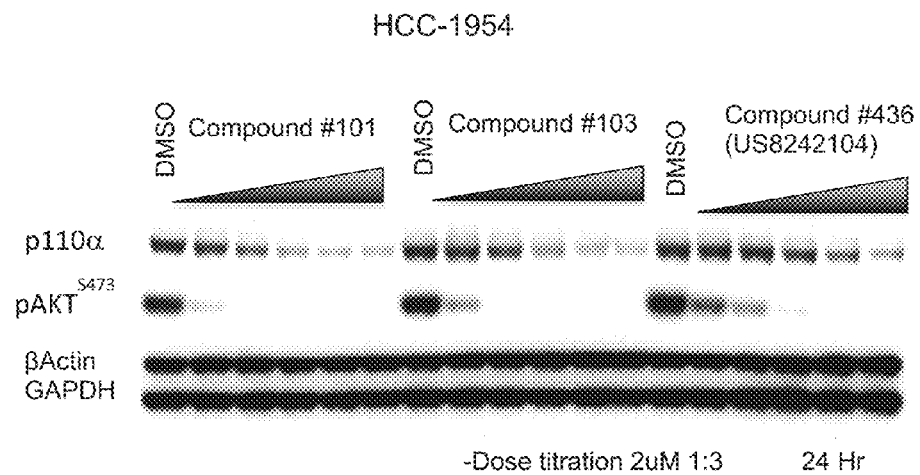
FIG. 3A shows Western-blot data depicting p110α (p110α, p110 alpha) levels after 24 hour treatment with Compound 101, Compound 103 and Compound 436 of U.S. Pat. No. 8,242,104 in HCC-1954 cells (PI3Kα mutant H1047R).
Figure 3B:
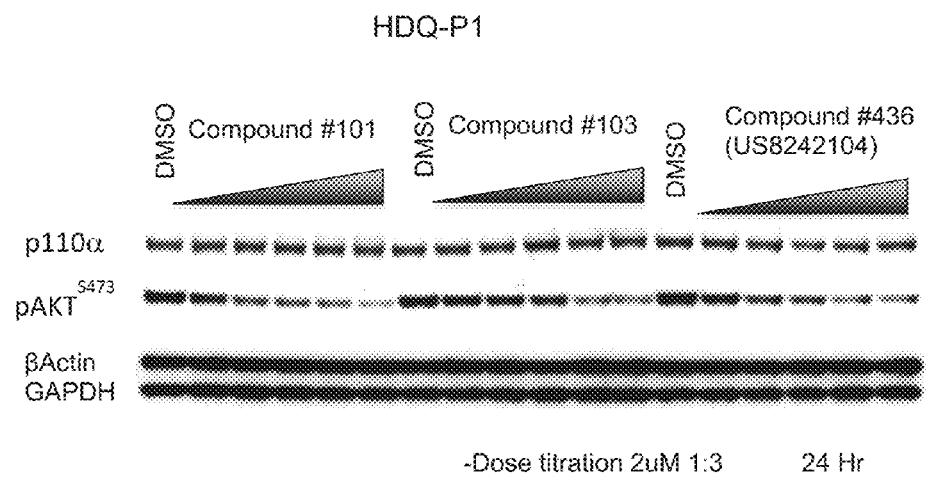
FIG. 3B shows Western-blot data depicting p110α (p110a, p110 alpha) levels after 24 hour treatment with Compound 101, Compound 103 and Compound 436 of U.S. Pat. No. 8,242,104 in HDQ-PI cells (PI3Kα wild-type).

The ability of a compound of the invention to decrease p110α levels was determined in experiments with HCC1954 (PI3Kα mutant H1047R) and HDQ-P1 (PI3Kα wild-type) lines, using the methods of Example 905. FIGS. 3A and 3B show representative Formula 1 compounds 101 and 103 able to promote reduction of p110α levels selectively in PI3K mutant (HCC1954, PI3Kα mutant H1047R) vs. PI3Kα wild-type (HDQ-P1, PI3Kα wild-type) tumor cells in a concentration dependent manner. FIG. 3A shows Western-blot data depicting p110α (p110α, p110 alpha) levels after 24 hour treatment with Compound 101, Compound 103 and Compound 436 of U.S. Pat. No. 8,242,104 in HCC-1954 cells (PI3Kα mutant H1047R). FIG. 3B shows Western-blot data depicting p110α (p110a, p110 alpha) levels after 24 hour treatment with Compound 101, Compound 103 and Compound 436 of U.S. Pat. No. 8,242,104 in HDQ-PI cells (PI3Kα wild-type). Compounds 101 and 103 more strongly influence p110α levels compared to compound-436 (U.S. Pat. No. 8,242,104).

Multiple Day Oral Dosing in Dogs

The ability of a compound of the invention to promote gastrointestinal and/or systemic inflammation or cause lymphoid depletion was assessed via clinical and anatomic pathology evaluation after multiple-day dosing in Beagle dogs (7-14 days). Formula 1 compounds 101 and 103 at >5-fold free exposure multiples over TGI60 (tumor growth inhibition 60% in a PI3K-mutant xenograft study) do not promote a pro-inflammatory signature as determined by clinical pathology or anatomic pathology evaluation (Table 11a, 11b). Similarly, compounds 101 and 103 produce only minor amounts of lymphoid depletion at high exposure multiples. In contrast, experiments with comparator compound taselisib indicate significant pro-inflammatory effects and lymphoid depletion at <0.3-fold free exposure over TGI60 (Table 11c). Comparator compounds alpelisib (BYL-719) and compound 436 (U.S. Pat. No. 8,242,104) also cause inflammation and lymphoid depletion at lower exposure multiples compared to Formula 1 compounds 101 and 103 (Table 11d, 11e). The extent and severity of findings is consistent with increased inhibition of PI3Kδ (delta) at exposure multiples over CD69 IC$_{50}$ for the comparator compounds.

TABLE 11

Multi day dosing of Formula 1 and comparator compounds in dog.

(a)

| Compound 101 Dose mg/kg/day QD | Exposure AUC0-24 hr, D14 (μM hr, total/free) | Cmax D14 (μM, total/free) | Cmin D14 (μM, total) | Exposure multiples* (total/free, AUC) | Exposure multiples to CD69 IC50** (total, $C_{min}$) | Clinical Signs | Clinical Pathology[+] | Histopathology[+] |
|---|---|---|---|---|---|---|---|---|
| 0.05 | 0.23/0.16 | 0.033/0.023 | 0.0046 | 0.2×/0.6× | 0.07× | — | — | — |
| 0.15 | 0.87/0.60 | 0.097/0.067 | 0.012 | 0.8×/2.3× | 0.2× | — | — | — |
| 0.5 | 2.0/1.38 | 0.31/0.21 | 0.017 | 1.9×/5.3× | 0.3× | — | — | — |

$F_u$ dog = 0.692;
$F_u$ mouse = 0.252 ($F_u$ = unbound fraction in species plasma)
*Exposure multiples using TGI60 from a 21-day KPL4 xenograft study; TGI60 @ 2 mg/kg, 1.04 μM hr total, 0.26 μM hr free
**a-IgM stimulated CD69 expression (whole-blood) $IC_{50}$ = 67 nM
[+]Findings related to inflammation and lymphoid organs (b)

| Compound 103 Dose mg/kg/day QD | Exposure AUC0-24 hr, D14 (μM hr, total/free) | Cmax D14 (μM, total/free) | Cmin D14 (μM, total) | Exposure multiples* (total/free, AUC) | Exposure multiples to CD69 $IC_{50}$** (total, $C_{min}$) | Clinical Signs | Clinical Pathology[+] | Histopathology[+] |
|---|---|---|---|---|---|---|---|---|
| 0.1 | 0.27/0.14 | 0.04/0.02 | 0.0048 | 0.2×/4.7× | 0.03× | — | — | — |
| 0.3 | 0.9/0.46 | 0.13/0.066 | 0.011 | 0.8×/15× | 0.08× | — | — | — |
| 1 | 2.54/1.29 | 0.31/0.16 | 0.034 | 2.2×/43× | 0.2× | Abnormal feces (soft/mucoid, 4/4) | ↓ lymphocytes | Lymphoid depletion: thymus |

$F_u$ dog = 0.507;
$F_u$ mouse = 0.03 ($F_u$ = unbound fraction in species plasma)
*Exposure multiples using TGI60 from a 21-day HCC1954 TGI study; TGI60 @ 3 mg/kg, 1.13 μM hr total, 0.03 μM hr free
**a-IgM stimulated CD69 expression (whole-blood) $IC_{50}$ = 142 nM
[+]Findings related to inflammation and lymphoid organs (c)

| taselisib Dose mg/kg/day QD | Exposure AUC0-24 hr, D7 (μM hr, total/free) | Cmax D7 (μM, total/free) | Cmin D7 (μM, total) | Exposure multiples* (total/free, AUC) | Exposure multiples to CD69 $IC_{50}$ (total, Cmin) | Clinical Signs | Clinical Pathology[+] | Histopathology[+] |
|---|---|---|---|---|---|---|---|---|
| 0.3 | 0.44/0.12 | 0.07/0.02 | 0.002 | 0.1×/0.3× | 0.7× | — | — | Lymphoid depletion: lymph nodes, GALT, spleen, thymus GI inflammation: Stomach, neutrophilic inflammation |
| 1 | 1.6/0.45 | 0.18/0.05 | 0.019 | 0.4×/1.0× | 6.2× | — | — | Lymphoid depletion: lymph nodes, GALT, spleen, thymus GI inflammation: Dark red areas in stomach & rectum corresponding to inflammation in stomach |
| 3 | 5.1/1.4 | 1.09/0.31 | 0.016 | 1.2×/3.2× | 5.2× | BW loss (7.9% vs pre-study; | ↓ lymphocytes ↑ neutrophils ↑ | Lymphoid depletion: lymph nodes, GALT, spleen, thymus |

TABLE 11-continued

Multi day dosing of Formula 1 and comparator compounds in dog.

|  |  |  |  |  | primarily 1 dog) thin, cool to touch (ears); abnormal feces; emesis | monocytes ↑ globulins ↓ A:G ratio ↑ fibrinogen | GI inflammation: Dark red areas in stomach & rectum corresponding to inflammation in stomach, rectum, cecum Systemic inflammation: Neutrophil infiltrates in lymph nodes, spleen, thymus, liver, lung, kidney |

$F_u$ dog = 0.28;
$F_u$ mouse = 0.10 ($F_u$ = unbound fraction in species plasma)
*Exposure multiples using TGI60 from a 21-day KPL4 xenograft study; TGI60 @ 4.3 uM hr (total) or 0.44 uM hr free
**a-IgM stimulated CD69 expression (whole-blood) $IC_{50}$ = 3.1 nM
†Findings related to inflammation and lymphoid organs (d)

| Compound 436 (U.S. Pat. No. 8,242,104) Dose mg/kg/day QD | Exposure AUC0-24 hr, D7 (μM hr, total/free) | Cmax D7 (μM, total/free) | Cmin D7 (μM, total) | Exposure multiples* (total/free, AUC) | Exposure multiples to CD69 $IC_{50}$** (total, Cmin) | Clinical Signs | Clinical Pathology† | Histopathology† |
|---|---|---|---|---|---|---|---|---|
| 0.5 | 3.4/2.3 | 0.68/0.46 | 0.016 | 1.2×/2.3× | 0.4× | — | — | Lymphoid depletion: thymus, lymph nodes |
| 2 | 15/10.2 | 2.5/1.7 | 0.059 | 5.4×/10.2× | 1.3× | — | ↑ fibrinogen ↑ globulins | Lymphoid depletion: thymus, lymph nodes, spleen, GALT |
| 6 | 56/38 | 6.8/4.6 | 0.408 | 20×/38× | 9.1× | BW loss (10% vs. pre-study) hypoactivity, excessive salivation, increased vomitus and abnormal feces | ↓ lymphocytes ↑ neutrophils ↑ fibrinogen ↑ globulins | Lymphoid depletion: thymus, lymph nodes, spleen, GALT GI inflammation: esophagus, stomach, colon, cecum Systemic inflammation: heart, aorta, meninges |

$F_u$ dog = 0.68;
$F_u$ mouse = 0.36 ($F_u$ = unbound fraction in species plasma)
*Exposure multiples using TGI60 from a 21-day KPL4 xenograft study; TGI60 @ 2.8 uM hr total, 1.0 uM hr free
**a-IgM stimulated CD69 expression (whole-blood) $IC_{50}$ = 45 nM
†Findings related to inflammation and lymphoid organs (e)

| alpelisib (BYL-719) Dose mg/kg/day QD | Exposure AUC0-24 hr, D7 (μM hr, total/free) | Cmax D7 (uM, total/free) | Cmin D7 (uM, total) | Exposure multiples* (total/free, AUC) | Exposure multiples to CD69 $IC_{50}$** (total, $C_{min}$) | Clinical Signs | Clinical Pathology† | Histopathology† |
|---|---|---|---|---|---|---|---|---|
| 3 | 14/1.0 | 1.97/0.14 | 0.20 | 0.2×/0.2× | 0.3× | — | — | — |
| 10 | 31.7/2.3 | 3.58/0.26 | 0.62 | 0.4×/0.4× | 1.0× | — | ↑ fibrinogen | GI inflammation: neutrophilic infiltrates, large intestine |

TABLE 11-continued

Multi day dosing of Formula 1 and comparator compounds in dog.

| | | | | | | | | |
|---|---|---|---|---|---|---|---|---|
| 30 | 160/11.5 | 20.6/1.5 | 1.25 | 2.2×/2.0× | 2.0× | ↓ appetite, ~10% ↓ BW | ↑ neutrophils ↑ monocytes ↑ globulins ↑ fibrinogen | Lymphoid depletion: thymus, lymph nodes, GALT GI inflammation: neutrophilic infiltrates in large and small intestine; rectal ulceration |

$F_u$ dog = 0.072;
$F_u$ mouse = 0.082 ($F_u$ = unbound fraction in species plasma)
*Exposure multiples using TGI60 from a 21-day KPL4 xenograft study; TGI60 @ 72 uM hr (total), 5.9 uM hr (free)
**a-IgM stimulated CD69 expression (whole-blood) $IC_{50}$ = 613 nM
+Findings related to inflammation and lymphoid organs Administration of Formula I Compounds The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 1 mg to about 10000 mg of Formula I compound. A typical dose may be about 10 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Formula I compounds of the present invention are useful for treating a human or animal patient suffering from a disease or disorder arising from abnormal cell growth, function or behavior associated with PI3K such as cancer, may thus be treated by a method comprising the administration thereto of a compound of the present invention as defined above. A human or animal patient suffering from cancer may also be treated by a method comprising the administration thereto of a compound of the present invention as defined above. The condition of the patient may thereby be improved or ameliorated.

Methods of the invention also include treating cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic myelogenous leukemia, lymphocytic leukemia, chronic lymphoid leukemia (CLL), myeloid leukemia, oral cavity and pharynx, non-Hodgkin lymphoma, melanoma and villous colon adenoma.

Based on expression analysis, immunohistochemical analysis and on cell line profiling, malignancies of the colon, breast, cervix, stomach, lung, and multiple myeloma are most likely to respond to PI3K modulators or inhibitors.

Pharmaceutical Formulations

In order to use a compound of this invention for the therapeutic treatment of mammals including humans, it is normally formulated in accordance with standard pharmaceutical practice as a pharmaceutical composition. According to this aspect of the invention there is to provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof.

The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of Formula I may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs. The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with additional therapeutic agents for the treatment of a disease or disorder described herein, such as inflammation or a hyperproliferative disorder (e.g., cancer). In certain embodiments, a compound of Formula I is combined in a pharmaceutical combination formulation, or dosing regimen as combination therapy, with an additional, second therapeutic compound that has anti-inflammatory or anti-hyperproliferative properties or that is useful for treating an inflammation, immune-response disorder, or hyperproliferative disorder (e.g., cancer). The additional therapeutic may be a Bcl-2 inhibitor, a JAK inhibitor, an anti-inflammatory agent, an immunomodulatory agent, chemotherapeutic agent, an apoptosis-enhancer, a neurotropic factor, an agent for treating cardiovascular disease, an agent for treating liver disease, an anti-viral agent, an agent for treating blood disorders, an agent for treating diabetes, and an agent for treating immunodeficiency disorders. The second therapeutic agent may be an NSAID anti-inflammatory agent. The second therapeutic agent may be a chemotherapeutic agent. The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, or a stereoisomer, tautomer, solvate, metabolite, or pharmaceutically acceptable salt or prodrug thereof, in combination with a therapeutic agent such as an NSAID.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound of Formula I, or a stereoisomer, tautomer, solvate, metabolite, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula I, or a stereoisomer, tautomer, solvate, metabolite, or pharmaceutically acceptable salt or prodrug thereof, and the use of at least one other cancer treatment method. The amounts of the compound(s) of Formula I and the other pharmaceutically active therapeutic agent(s) and the relative timings of administration will be selected in order to achieve the desired combined therapeutic effect.

Additional therapeutic agents employed in combination with a compound of Formula I include 5-FU, docetaxel, eribulin, gemcitabine, cobimetinib, ipatasertib, paclitaxel, tamoxifen, fulvestrant, GDC-0810, dexamethasone, palbociclib, bevacizumab, pertuzumab, trastuzumab emtansine, trastuzumab and letrozole.

Metabolites of Compounds of Formula I

Also falling within the scope of this invention are the in vivo metabolic products of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. In one embodiment, the kit comprises a container comprising a compound of Formula I. or a stereoisomer, tautomer, solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I Compounds

Compounds of Formula I may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12): 1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen*

*Chemie*, 4, Aufl. ed. Springer-Verlag, Berlin, including supplements (also available via the Beilstein online database).

Synthetic chemistry transformations and protecting group methodologies (protection and deprotection) useful in synthesizing Formula I compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

The Examples provide exemplary methods for preparing Formula I compounds. Those skilled in the art will appreciate that other synthetic routes may be used to synthesize the Formula I compounds. Although specific starting materials and reagents are depicted and discussed in the Figures and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

In the methods of preparing Formula I compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Compounds of the invention were prepared as illustrated in general Schemes 1 and 2.

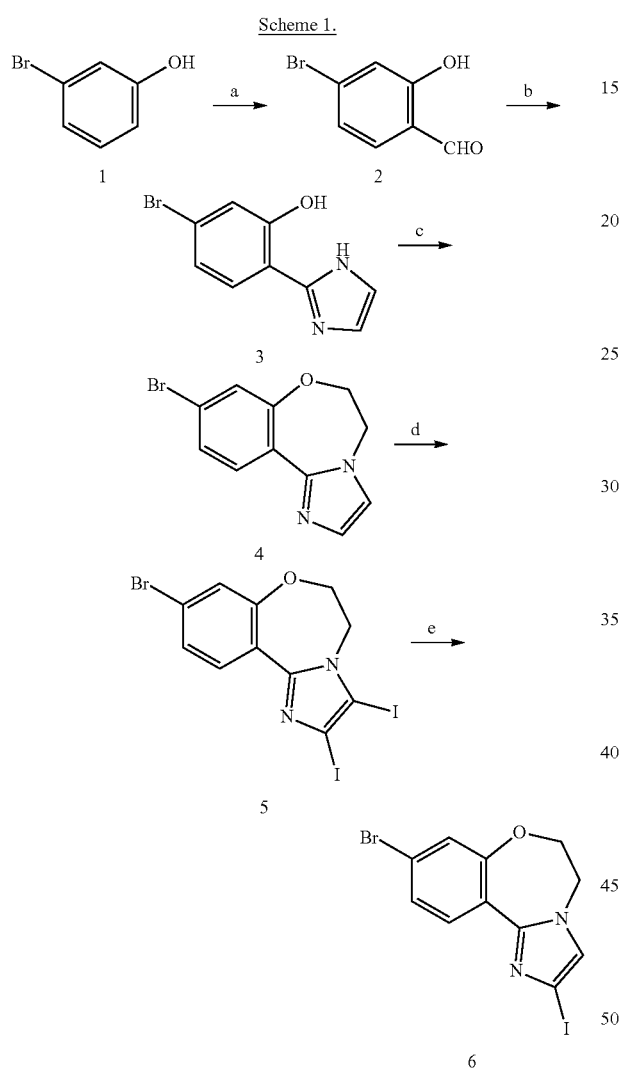

a) MgCl$_2$, triethylamine, paraformaldehyde, acetonitrile, heat; b) oxaldehyde, ammonium hydroxide, heat; c) cesium carbonate, 1,2-dibromoethane, DMF, heat; d) N-iodosuccinimide, DMF, heat; e) i. EtMgBr, THF, −20° C., ii. aqueous ammonium chloride As shown in Scheme 1, 4-bromo-2-hydroxybenzaldehyde 2 may be obtained by formylating commercially available 3-bromophenol. Heating 2 with oxaldehyde and ammonium hydroxide affords 3. The oxazepin ring may be formed by heating 3 with 1,2-dibromoethane. Bis iodination may be induced by reaction with N-iodosuccinimide, and the 3-iodo group selectively removed through treatment with ethyl magnesium bromide at reduced temperature, to afford 6.

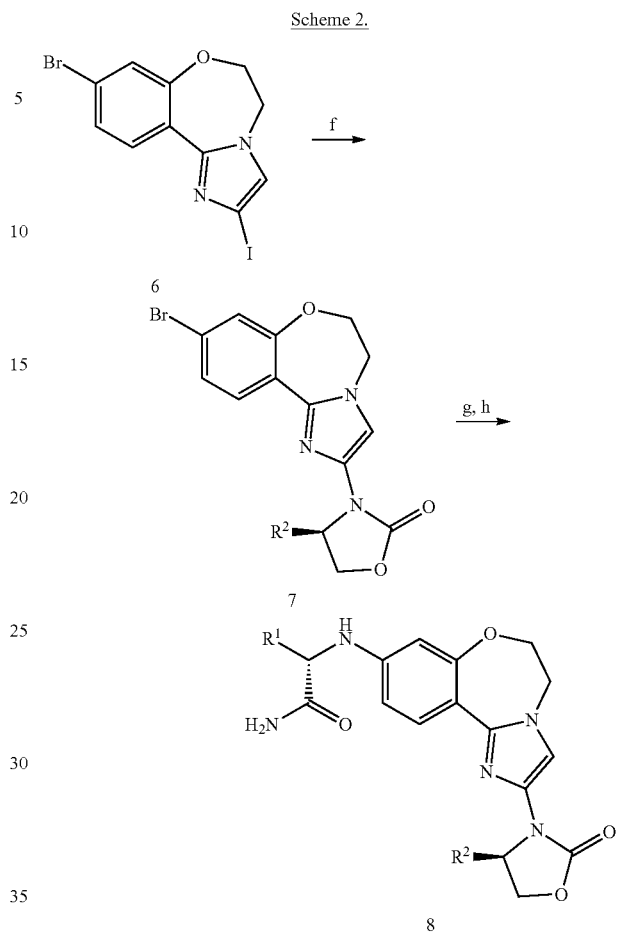

f) 4-substituted oxazolidin-2-one, Cu(OAc)$_2$, trans-N,N'-dimethylcyclohexane-1,2-diamine, potassium carbonate, dioxane, heat; g) HN(R$^2$)CH(R$^1$)CO$_2$H, CuI, K$_3$PO$_4$, DMSO, heat; h) ammonium chloride, triethylamine, HATU (1-[Bis(dimethylamino)methylene]-1H-1,2,3-triazolo[4,5-b]pyridinium 3-oxide hexafluorophosphate)

As shown in Scheme 2, 6 may be coupled to an appropriately substituted oxazolidin-2-one using copper catalysis to provide 7. Bromo intermediate 7 may be coupled to appropriately substituted amino acids under copper catalysis, followed by HATU-mediated amide coupling with ammonium chloride to provide compounds 8.

EXAMPLES

Abbreviations

DMSO Dimethyl sulfoxide
ESI Electrospray ionization
HPLC High pressure liquid chromatography
LCMS Liquid chromatography mass spectrometry
min Minutes
N Normal
NMR Nuclear magnetic resonance
R$_T$ Retention time LCMS Method A: Experiments performed on a Waters Micromass ZQ2000 quadrupole mass spectrometer linked to a Waters Acquity UPLC system with a PDA UV detector. The spectrometer has an electrospray source operating in positive and negative ion mode. This system uses an Acquity BEH C18 1.7 um 100×2.1 mm column, maintained at 40° C. or an Acquity BEH Shield RP18 1.7 μm 100×2.1 mm column, maintained at 40° C. and a 0.4 mL/minute flow rate. The initial solvent system was 95% water containing 0.1% formic acid (solvent A) and 5% acetonitrile containing 0.1% formic acid (solvent B) for the first 0.4 minute followed by a gradient up to 5% solvent A and 95% solvent B over the next 5.6 minutes. This was maintained for 0.8 minutes before returning to 95%0/solvent A and 5% solvent B over the next 0.2 minutes. Total run time was 8 minutes.

LCMS Method B: Experiments performed on an Agilent 1100 HPLC coupled with Agilent MSD mass spectrometer using ESI as ionization source. The LC separation was using a Phenomenex XB-C18, 1.7 mm, 50×2.1 mm column with a 0.4 mL/minute flow rate. Solvent A is water with 0.1% formic acid and solvent B is acetonitrile with 0.1% formic acid. The gradient consisted with 2-98% solvent B over 7 minutes and hold 97% B for 1.5 minutes following equilibration for 1.5 minutes. LC column temperature is 40° C. UV absorbance was collected at 220 nm and 254 nm and mass spec full scan was applied to all experiments.

Example 101 (S)-2-((2-((S)-4-(Difluoromethyl)-2-oxooxazolidin-3-yl)-5,6-dihydrobenzo[f]imidazo[1,2-d][1,4]oxazepin-9-yl)amino)propanamide 101

Step 1: 4-Bromo-2-hydroxybenzaldehyde

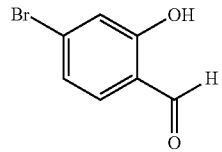

Into a 20 L 4-necked round-bottom flask purged and maintained with an inert atmosphere of nitrogen was placed 3-bromophenol (1300 g, 7.51 mol), dichloromagnesium (1078 g, 11.3 mol), triethylamine (3034 g, 30.0 mol) and acetonitrile (7.8 L). The mixture was stirred for 30 minutes at 40° C. To the mixture was added paraformaldehyde (676 g, 22.6 mol) at 80° C. The resulting solution was stirred for 6 hours at 76° C. This reaction was repeated 5 times. The combined reaction mixtures were quenched by the addition of 12 L of aqueous hydrogen chloride (4 N). The pH value of the solution was adjusted to 5 with concentrated aqueous hydrogen chloride (12 N). The resulting solution was extracted with 1×20 L of ethyl acetate. The organic extracts were evaporated in vacuo. The residue was purified via flash chromatography on silica gel (eluted: 15% ethyl acetate in petroleum ether) to give crude product which was washed with 2.4 L of methyl tert-butyl ether:hexane (1:4). The resultant solids were collected by filtration to yield 7.0 kg (78%) of the title compound as a yellow solid.

Step 2: 5-Bromo-2-(1H-imidazol-2-yl)phenol

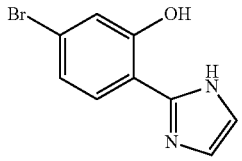 [SMILES: Oc1cc(Br)ccc1-c1ncc[nH]1]

Into a 20 L 4-necked round-bottom flask was placed a solution of 4-bromo-2-hydroxybenzaldehyde (700 g, 3.50 mol) in methanol (7.0 L) and oxaldehyde (40%) (2540 g, 17.5 mol) followed by the dropwise addition over 4 hours of aqueous ammonia (25-28%, 3500 g) with stirring and maintaining the temperature below 40° C. The resulting solution was stirred for 15 hours at 30-35° C. This reaction was repeated 9 times. The combined 9 reaction mixtures were evaporated in vacuo keeping the temperature below 45° C. The residue was diluted with 100 L of ethyl acetate with stirring for 30 minutes. The solids were filtered out and the resulting solution was diluted with water. The aqueous phase was extracted with 35 L of ethyl acetate. The organic extracts were evaporated under vacuum and the residue was purified via flash chromatography on silica gel (solvent gradient: 5-75% ethyl acetate in petroleum ether) to yield 2.4 kg (29%) of the title compound as a yellow solid.

Step 3: 9-Bromo-5,6-dihydrobenzo[f]imidazo[1,2-d][1,4]oxazepine

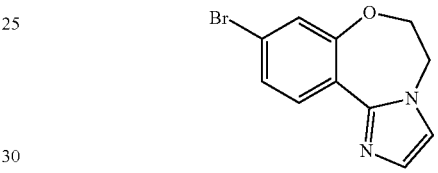

Into a 20 L 4-necked round-bottom flask was placed a solution of 5-bromo-2-(1H-imidazol-2-yl)phenol (1.4 kg, 5.86 mol) in N,N-dimethylformamide (14 L) and cesium carbonate (7.2 kg, 22.1 mol). The mixture was stirred for 20 minutes. To the reaction mixture was added 1,2-dibromoethane (4.1 kg, 21.8 mol). The resulting solution was stirred for 4-12 hours at 85-90° C., cooled to 15° C., and filtered. The filter cake was washed with 3.0 L of ethyl acetate. The filtrate was diluted with 14 L of ethyl acetate. The combined organic extracts were washed with brine (4×14 L), dried over anhydrous sodium sulfate, filtered and evaporated in vacuo to yield 1.1 kg (71%) of the title compound as a light yellow solid. LCMS (ESI): [M+H]$^+$=265; $^1$H NMR (400 MHz, DMSO-d$_6$) δ 8.32 (d, J=8.4, 1H), 7.35-7.24 (m, 3H), 7.06 (s, 1H), 4.47-4.42 (m, 4H).

Step 4: 9-Bromo-2,3-diiodo-5,6-dihydrobenzo[f]imidazo[1,2-d][1,4]oxazepine

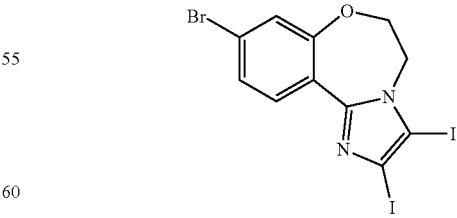

Into a 20 L 4-necked round-bottom flask was placed 9-bromo-5,6-dihydrobenzo[f]imidazo[1,2-d][1,4]oxazepine (2.5 kg, 9.43 mol) and N,N-dimethylformamide (12.5 L) followed by the addition of N-iodosuccinimide (6.0 kg, 26.7 mol) in several batches with stirring. The resulting solution was stirred for 12 hours at 60° C., cooled to 15° C. with a water/ice bath, diluted with 12.5 L of water/ice, and filtered. The filtered solids were recrystallized from petroleum ether to yield 4.0 kg (82%) of the title compound as a yellow solid.

Step 5: 9-Bromo-2-iodo-5,6-dihydrobenzo[f]imidazo[1,2-d][1,4]oxazepine

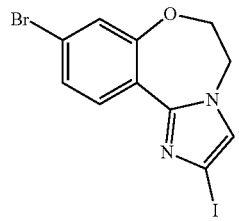 [SMILES: Brc1ccc2c(c1)OCCn1cc(I)nc1-2]

To a 20 L 4-necked round-bottom flask purged and maintained with an inert atmosphere of nitrogen was placed 9-bromo-2,3-diiodo-5,6-dihydrobenzo[f]imidazo[1,2-d]j[1,4]oxazepine (800 g, 1.55 mol) and tetrahydrofuran (2.4 L) followed by the dropwise addition of ethyl magnesium bromide (1 N solution in ether, 1.7 L) with stirring at −20° C., over 3.5 hours. The reaction mixture was stirred for 3 hours keeping the temperature at −15° C. using an ice/salt bath. The resultant mixture was quenched by the addition of 3.0 L of saturated aqueous ammonium chloride, and extracted with ethyl acetate (2×8.0 L). The combined organic extracts were washed with brine (2×10 L), dried over anhydrous sodium sulfate, filtered and evaporated in vacuo. The crude residue was triturated with 8.0 L of ethyl acetate:petroleum ether (1:5), filtered, and washed with petroleum ether to yield 501 g (83%) of the title compound as a brown solid. LCMS (ESI): [M+H]$^+$=391; $^1$H NMR (400 MHz, DMSO-d$_6$) δ 8.22 (d, J=8.7, 1H), 7.55 (s, 1H), 7.30-7.25 (m, 2H), 4.45-4.41 (m, 4H).

Step 6: (R)-2,2-Dimethyl-[1,3]dioxolane-4-carbaldehyde

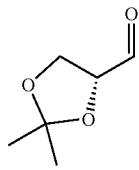

Sodium periodate (57.0 g, 270 mmol) was dissolved in hot water (115 mL) and silica (200 g, 60 Å 220-440 mesh, particle size 35-75 μm) was added. The mixture was stirred vigorously until a free flowing powder was obtained. This was added to a solution of 1,2:5,6-bis-O-(1-methylethylidene)-D-mannitol (50 g, 190 mmol) in dichloromethane (1.0 L) and the reaction was stirred at room temperature for 1 hour. The resultant mixture was filtered through a pad of Na$_2$SO$_4$ and the solids washed thoroughly with dichloromethane. The combined organic extracts were evaporated in vacuo to yield 37.2 g (75%) of the title compound as a colorless oil. $^1$H NMR (400 MHz, CDCl$_3$) δ 9.73 (d, J=1.9 Hz, 1H), 4.38 (ddd, J=7.4, 4.7, 1.9 Hz, 1H), 4.18 (dd, J=8.8, 7.4 Hz, 1H), 4.10 (dd, J=8.8, 4.7 Hz, 1H), 1.49 (s, 3H), 1.43 (s, 3H).

Step 7: (R)-4-Difluoromethyl-2,2-dimethyl-[1,3]dioxolane

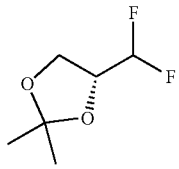

To a solution of (R)-2,2-dimethyl-[1,3]dioxolane-4-carbaldehyde (7.08 g, 54 mmol) in dichloromethane (50 mL) cooled in a water bath was added, dropwise, diethylaminosulfur trifluoride (8.4 mL, 62.6 mmol) and the reaction mixture was stirred at room temperature for 3 hours. The resultant mixture was added dropwise to a rapidly stirring, ice cold saturated aqueous sodium bicarbonate solution. The mixture was further extracted with dichloromethane. The combined organic extracts were washed with brine, dried over magnesium sulfate, filtered and evaporated in vacuo to yield 6.58 g (79%) of the crude title compound as an orange oil. $^1$H NMR (400 MHz, CDCl$_3$) δ 5.69 (td, J=55.8, 4.9 Hz, 1H), 4.27-4.17 (m, 1H), 4.16-4.03 (m, 2H), 1.46 (s, 3H), 1.38 (s, 3H).

Step 8: (R)-3-(tert-Butyldimethylsilanyloxy)-1,1-difluoropropan-2-ol

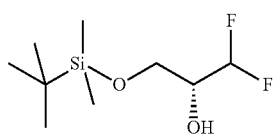

HCl in dioxane (4 N, 10.8 mL, 43.2 mmol) was added to a solution of (R)-4-difluoromethyl-2,2-dimethyl[1,3]dioxolane (6.58 g, 43.2 mmol) in methanol (40 mL) and the reaction mixture was stirred at room temperature for 30 minutes. The resultant mixture was evaporated in vacuo and azeotroped with acetonitrile. The residue was dissolved in N,N-dimethylformamide (10 mL) and tert-butyldimethylsilyl chloride (6.53 g, 43.2 mmol), triethylamine (9.0 mL, 64.9 mmol) and 4-(dimethylamino)pyridine (catalytic) were added. The reaction mixture was stirred at room temperature for 1 hour. The resultant mixture was washed with water and then extracted with dichloromethane. The combined organic extracts were washed with brine, dried over magnesium sulfate, filtered and evaporated in vacuo. The resultant crude residue was purified via flash chromatography on silica gel (solvent gradient: 0-30% ethyl acetate in cyclohexane) to yield 3.43 g (35%) of the title compound as a yellow oil. $^1$H NMR (400 MHz, CDCl$_3$) 5.66 (td, J=56.4, 4.6 Hz, 1H), 3.76-3.60 (m, 2H), 2.46 (d, J=6.4 Hz, 1H), 0.81 (s, 9H), 0.00 (s, 6H).

Step 9: ((S)-2-Azido-3,3-difluoropropoxy)-tert-butyldimethylsilane

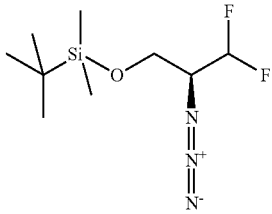 [SMILES: CC(C)(C)[Si](C)(C)OC[C@H](N=[N+]=[N-])C(F)F]

Trifluoromethanesulfonic anhydride (2.9 mL, 17.4 mmol) was added dropwise to a solution of (R)-3-(tert-butyldimethylsilanyloxy)-1,1-difluoropropan-2-ol (3.43 g, 15.1 mmol) and pyridine (2.0 mL, 24.2 mmol) in dichloromethane (50 mL) at −20° C. and the reaction mixture stirred at −20° C. for 20 minutes and then at 0° C. for 1 hour. The resultant mixture was diluted with 0.5 N aqueous HCl and extracted with dichloromethane. The combined organic extracts were dried over magnesium sulfate and evaporated in vacuo. The crude residue was dissolved in N,N-dimethylformamide (10 mL), sodium azide (2.96 g, 45.5 mmol) was added and the reaction mixture was stirred at room temperature for 2 hours. The resultant mixture was diluted with water and extracted with ethyl acetate. The combined organic extracts were washed with brine, dried over magnesium sulfate, filtered and evaporated in vacuo to yield 4.50 g of the crude title compound. $^1$H NMR (400 MHz, CDCl$_3$) δ 5.74 (td, J=55.4, 4.4 Hz, 1H), 3.81-3.71 (m, 2H), 3.58-3.47 (m, 1H), 0.81 (s, 9H), 0.00 (s, 6H).

Step 10: (S)-1-(tert-Butyldimethylsilanyloxymethyl)-2,2-difluoroethylamine

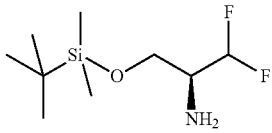

Palladium hydroxide on carbon (200 mg, 20%) was added to a solution of ((R)-2-azido-3,3-difluoropropoxy)-tert-butyldimethylsilane (4.50 g, crude, assume ~15.1 mmol) in ethyl acetate (20 mL) and methanol (2.0 mL) and the reaction stirred under a balloon of hydrogen for 16 hours. The reaction was filtered, fresh palladium hydroxide on carbon (400 mg, 20%) added and the reaction mixture was stirred under a balloon of hydrogen for 16 hours. The resultant mixture was filtered and the filtrate was evaporated in vacuo to yield 3.08 g (90%) of the crude title product as a colorless oil. $^1$H NMR (400 MHz, CDCl$_3$) δ 5.66 (td, J=57.0, 4.7 Hz, 1H), 3.71-3.57 (m, 2H), 3.00-2.89 (m, 1H), 1.42 (br s, 2H), 0.82 (s, 9H), 0.00 (s, 6H).

Step 11: (S)-4-Difluoromethyloxazolidin-2-one

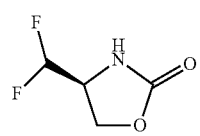

HCl in dioxane (4 N, 5.0 mL, 20 mmol) was added to a solution of (R)-1-(tert-butyldimethylsilanyloxymethyl)-2,2-difluoroethylamine (Org. Lett., Vol. 9, No. 1, 2007, 41-44) (2.30 g, 10.3 mmol) in methanol (5.0 mL) and the reaction mixture was stirred at room temperature for 2 hours. The mixture was evaporated in vacuo and the resultant oil was triturated with diethyl ether to give a solid which was dried in vacuo. The solid was dissolved in a mixture of toluene (20 mL) and KOH (2.50 g, 44.6 mmol in 20 mL water) at 0° C. Phosgene (16.3 mL, 20% in toluene) was added dropwise, the cooling bath was removed and the reaction mixture was stirred for 1 hour. The mixture was evaporated in vacuo, the resultant residue was extracted with hot industrial methylated spirits and the solid was collected by filtration. The filtrate was evaporated in vacuo and the resultant residue was purified via flash chromatography on silica gel (solvent gradient: 0-100% ethyl acetate in cyclohexane) to yield 830 mg (68%) of the title compound as an off-white solid. [α]$_D$=+10.1 (c=2.37, CHCl$_3$). $^1$H NMR (400 MHz, CDCl$_3$) δ 5.96 (br s, 1H), 5.78 (td, J=55.3, 4.8 Hz, 1H), 4.54 (t, J=9.2 Hz, 1H), 4.42 (dd, J=9.6, 4.4 Hz, 1H), 4.17-4.06 (m, 1H).

Step 12: (S)-3-(9-Bromo-5,6-dihydrobenzo[f]imidazo[1,2-d][1,4]oxazepin-2-yl)-4-(difluoromethyl)oxazolidin-2-one

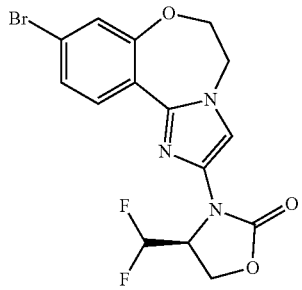 [SMILES: O=C1OC[C@@H](C(F)F)N1c1cn2c(n1)-c1ccc(Br)cc1OCC2]

A mixture of 9-bromo-2-iodo-5,6-dihydrobenzo[f]imidazo[1,2-d][1,4]oxazepine (250 mg, 0.64 mmol), (S)-4-difluoromethyloxazolidin-2-one (88 mg, 0.64 mmol), trans-N,N'-dimethyl-1,2-cyclohexane diamine (36 mg, 0.26 mmol), cuprous iodide (24 mg, 0.13 mmol) and potassium carbonate (177 mg, 1.28 mmol) in dioxane (3.0 mL) was degassed with argon under sonication. The reaction mixture was heated at 100° C. for 5 h and then allowed to cool to room temperature. The resultant mixture was diluted with 15% aqueous ammonia and extracted with ethyl acetate. The combined organic extracts were washed with brine, dried over magnesium sulfate, filtered and evaporated in vacuo. The resultant residue was triturated with methanol and then purified via preparative HPLC [C18, 60% acetonitrile (0.1% formic acid) in water (0.1% formic acid), 20 minute run] to yield 20 mg (8%) of the title compound as a white solid. LCMS (ESI): [M+H]$^+$=400/402. $^1$H NMR (400 MHz, CDCl$_3$) δ 8.19 (d, J=9.2 Hz, 1H), 7.29 (s, 1H), 7.24-7.19 (m, 2H), 6.65 (ddd, J=57.8, 54.5, 1.0 Hz, 1H), 4.87 (ddd, J=24.0, 9.2, 4.0 Hz, 1H), 4.73 (dd, J=9.5, 4.2 Hz, 1H), 4.53 (t, J=9.2 Hz, 1H), 4.48-4.43 (m, 2H), 4.38-4.33 (m, 2H).

Step 13: (S)-2-((2-((S)-4-(Difluoromethyl)-2-oxooxazolidin-3-yl)-5,6-dihydrobenzo[f]imidazo[1,2-d][1,4]oxazepin-9-yl)amino)propanamide (S)-3-(9-Bromo-5,6-dihydrobenzo[f]imidazo[1,2-d][1,4]oxazepin-2-yl)-4-(difluoromethyl)oxazolidin-2-one (600 mg, 1.50 mmol), L-alanine (267 mg, 3.00 mmol), cuprous iodide (57 mg, 0.30 mmol) and potassium phosphate tribasic (637 mg, 3.00 mmol) were suspended in dimethyl sulfoxide (6.0 mL). The reaction mixture was heated at 100° C. for 2 hours. Upon allowing to cool to room temperature, dimethyl sulfoxide (4.0 mL), ammonium chloride (480 mg, 9.00 mmol), and triethylamine (3.1 mL, 22.5 mmol) were added. To the resultant stirred suspension was added, 1-[bis(dimethylamino)methylene]-1H-1,2,3-triazolo[4,5-b]pyridinium 3-oxide hexafluorophosphate (5.10 g, 13.5 mmol), portionwise over 5 minutes. The reaction mixture was stirred at room temperature for 1 hour and then filtered through Celite®, washing with ethyl acetate. The organic extracts were washed with saturated aqueous sodium bicarbonate and the aqueous phase was extracted with ethyl acetate. The combined organic extracts were washed with brine, dried over sodium sulfate, filtered and evaporated in vacuo. The crude residue was purified via flash chromatography on silica gel (solvent gradient: 0-5% methanol in dichloromethane) and then by chiral supercritical fluid chromatography to yield 294 mg (46%) of 101 as an off-white solid. LCMS (ESI): R$_T$ (min)=2.89 [M+H]$^+$=408, Method=A; $^1$H NMR (400 MHz, DMSO-d$_6$) δ 8.00 (d, J=8.7 Hz, 1H), 7.38 (br s, 1H), 7.18 (s, 1H), 7.00 (br s, 1H), 6.71 (t, J=55.9 Hz, 1H), 6.41 (dd, J=8.8, 2.3 Hz, 1H), 6.16 (d, J=7.2 Hz, 1H), 6.09 (d, J=1.9 Hz, 1H), 5.02-4.89 (m, 1H), 4.63-4.52 (m, 2H), 4.39-4.30 (m, 4H), 3.76 (quintet, J=7.0 Hz, 1H), 1.30 (d, J=7.1 Hz, 3H).

Example 102 (S)-2-cyclobutyl-2-((2-((R)-4-methyl-2-oxooxazolidin-3-yl)-5,6-dihydrobenzo[f]imidazo[1,2-d][1,4]oxazepin-9-yl)amino)acetamide 102

Step 1: (R)-4-Methyloxazolidin-2-one

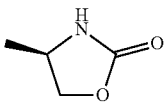

To a mixture of D-alaninol (8.65 g, 0.12 mmol) in toluene and aqueous KOH (124 mL, 12.5% aq, 0.28 mmol) at 0° C. was added phosgene (72.7 mL, 20% in toluene, 0.14 mmol) at such a rate that the internal temperature remained <5° C. The reaction mixture was stirred at 0° C. for a further 40 minutes then evaporated to dryness. The crude residue was extracted with industrial methylate spirits, the slurry was filtered and the filtrate evaporated in vacuo. The resultant residue was purified via flash chromatography on silica gel (solvent gradient: 40-100% ethyl acetate in cyclohexane) to yield 10.4 g (90%) of the title compound as a white solid. $^1$H NMR (400 MHz, CDCl$_3$) δ 6.00 (br s, 1H), 4.50 (t, J=6.5 Hz, 1H), 4.07-3.97 (m, 1H), 3.95 (dd, J=7.8, 6.2 Hz, 1H), 1.30 (d, J=6.1 Hz, 3H).

Step 2: (R)-3-(9-Bromo-5,6-dihydrobenzo[f]imidazo[1,2-d][1,4]oxazepin-2-yl)-4-methyloxazolidin-2-one and (R)-3-(9-Iodo-5,6-dihydrobenzo[f]imidazo[1,2-d][1,4]oxazepin-2-yl)-4-methyloxazolidin-2-one

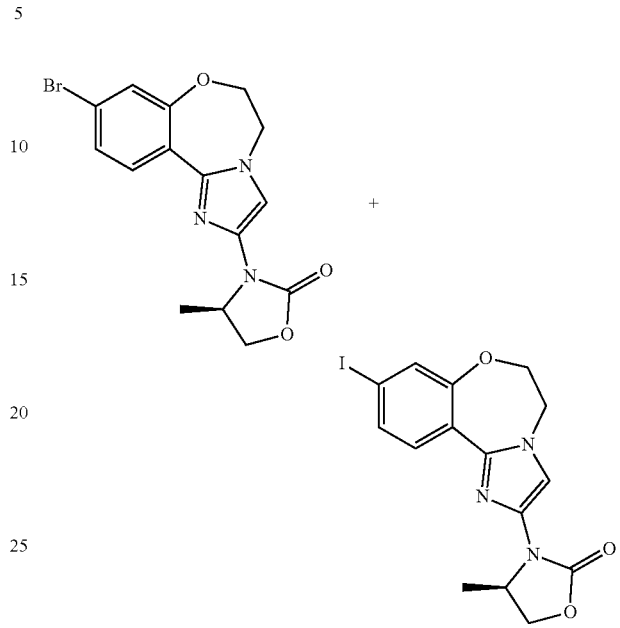

A mixture of 9-bromo-2-iodo-5,6-dihydrobenzo[f]imidazo[1,2-d][1,4]oxazepine (30.0 g, 76.7 mmol), (R)-4-methyloxazolidin-2-one (7.70 g, 76.7 mmol), cuprous iodide (1.61 g, 8.40 mmol), trans-N,N'-dimethyl-1,2-cyclohexane diamine (2.7 mL, 16.9 mmol) and potassium carbonate (14.9 g, 107 mmol) were suspended in 1,4-dioxane (200 mL) and the reaction mixture degassed with argon under sonication. The resultant mixture was heated at 100° C. for 16 h. The reaction mixture was diluted with aqueous ammonia solution (~16%) and extracted with ethyl acetate. The combined organic extracts were washed with brine, dried over magnesium sulfate, filtered and evaporated in vacuo. The resultant residue was purified via flash chromatography on silica gel (solvent gradient: 0-100% ethyl acetate in cyclohexane) to yield 13.4 g (~42%) of the title compounds (~2:1 mixture of 9-Br:9-I products). $^1$H NMR (400 MHz, CDCl$_3$) δ 8.28 (d, J=7.6 Hz, 0.33H), 8.11 (d, J=6.9 Hz, 0.66H), 7.42-7.38 (m, 1H), 7.28-7.24 (m, 1.33H), 7.23-7.18 (m, 0.66H), 4.77-4.68 (m, 1H), 4.58 (t, J=8.3 Hz, 1H), 4.49-4.39 (m, 2H), 4.37-4.30 (m, 2H), 4.08 (dd, J=8.4, 4.5 Hz, 1H), 1.57-1.50 (m, 3H).

Step 3: (R)-3-(9-Bromo-5,6-dihydroimidazo[1,2-d][1,4]benzoxazepin-2-yl)-4-methyl-oxazolidin-2-one

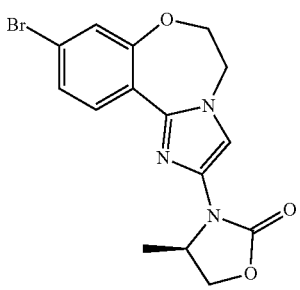 [SMILES: C[C@@H]1COC(=O)N1c1cn2c(n1)-c1ccc(Br)cc1OCC2]

80 mg of a mixture of (R)-3-(9-Bromo-5,6-dihydrobenzo[f]imidazo[1,2-d][1,4]oxazepin-2-yl)-4-methyloxazolidin-2-one and (R)-3-(9-Iodo-5,6-dihydrobenzo[f]imidazo[1,2-d][1,4]oxazepin-2-yl)-4-methyloxazolidin-2-one was separated via chiral SFC, to yield 27.6 mg of the title compound. LCMS (ESI): [M+H]$^+$=364.0/366.0/367.2; $^1$H NMR (400 MHz, DMSO-d$_6$) δ 8.22 (d, J=8.7 Hz, 1H), 7.35 (s, 1H), 7.31 (dd, J=8.7, 2.1 Hz, 1H), 7.25 (d, J=2.0 Hz, 1H), 4.65-4.54 (m, 2H), 4.49-4.43 (m, 4H), 4.09-4.06 (m, 1H), 1.42 (d, J=6.0 Hz).

Step 4: Methyl (S)-2-cyclobutyl-2-((2-((R)-4-methyl-2-oxooxazolidin-3-yl)-5,6-dihydrobenzo[]imidazo[1,2-d][1,4]oxazepin-9-yl)amino)acetate

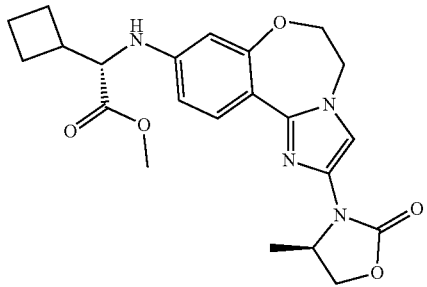 [SMILES: COC(=O)[C@@H](Nc1ccc2c(c1)OCCn1cc(N3C(=O)OC[C@H]3C)nc1-2)C1CCC1]

A mixture of (4R)-3-(9-bromo-5,6-dihydroimidazo[1,2-d][1,4]benzoxazepin-2-yl)-4-methyl-oxazolidin-2-one (0.2746 mmol, 100 mg), cuprous iodide (0.084 mmol, 16 mg), (2S)-2-amino-2-cyclobutyl-acetic acid (1.10 mmol, 142 mg) and potassium phosphate tribasic (1.37 mmol, 297 mg) in dimethyl sulfoxide (3 mL) were heated under microwave irradiation at 120° C. for 2 hours. The reaction was cooled to room temperature, and iodomethane (1.4 mmol, 0.086 mL) was added and the reaction was extracted with dichloromethane and water. The combined organic extracts were combined, washed with brine, and dried with sodium sulfate, filtered and evaporated in vacuo. The crude product was purified via flash chromatography on silica gel (24 g silica, solvent gradient: 5-40% 3:1 isopropyl acetate:methanol in dichloromethane) to yield 100 mg (85%) of the title compound.

Step 5: (S)-2-cyclobutyl-2-((2-((R)-4-methyl-2-oxooxazolidin-3-yl)-5,6-dihydrobenzo[f]imidazo[1,2-d][1,4]oxazepin-9-yl)amino)acetamide To a solution of methyl (2S)-2-cyclobutyl-2-[[2-[(4R)-4-methyl-2-oxo-oxazolidin-3-yl]-5,6-dihydroimidazo[1,2-d][1,4]benzoxazepin-9-yl]amino]acetate (0.234 mmol, 100 mg) in tetrahydrofuran (5 mL) was added water (0.45 mL) and lithium hydroxide monohydrate (0.357 mmol, 15 mg). The reaction mixture was stirred at room temperature for 6 hours. The reaction mixture was evaporated in vacuo. To a solution of the resulting residue in N,N-dimethylformamide (3 mL) was added 1-[bis(dimethylamino)methylene]-1H-1,2,3-triazolo[4,5-b]pyridinium 3-oxide hexafluorophosphate (0.353 mmol, 137 mg), ammonium chloride (0.71 mmol, 38 mg) and N,N-diisopropylethylamine (0.705 mmol, 0.123 mL) and the reaction mixture stirred at room temperature for 1 hour. The reaction mixture was evaporated in vacuo and the resultant residue treated with water then extracted with dichloromethane. The combined organic extracts were washed with brine, dried over magnesium sulfate and evaporated in vacuo. The crude product was purified via reverse-phase HPLC, followed by SFC and lyophilized to yield 15.0 mg (15%) of 102. LCMS (ESI): R$_T$ (min)=3.03, [M+H]$^+$=412.2, method=D; $^1$H NMR (400 MHz, DMSO-d$_6$) δ 7.96 (d, J=8.8 Hz, 1H), 7.39-7.36 (brs, 1H), 7.13 (s, 1H), 7.00-6.97 (brs, 1H), 6.44 (dd, J=8.9, 2.3 Hz, 1H), 6.14 (d, J=2.3 Hz, 1H), 5.96 (d, J=7.7 Hz, 1H), 4.62-4.49 (m, 2H), 4.38-4.28 (m, 4H), 4.06-4.03 (m, 1H), 3.70-3.61 (m, 1H), 2.06-1.75 (m, 6H), 1.42-1.34 (m, 3H).

Example 103 (S)-2-Cyclopropyl-2-((2-((S)-4-(difluoromethyl)-2-oxooxazolidin-3-yl)-5,6-dihydrobenzo[f]imidazo[1,2-d][1,4]oxazepin-9-yl)amino)acetamide 103

A mixture of (S)-3-(9-bromo-5,6-dihydrobenzo[f]imidazo[1,2-d][1,4]oxazepin-2-yl)-4-(difluoromethyl)oxazolidin-2-one from Example 101, step 12 (400 mg, 1.00 mmol), L-cyclopropylglycine (230 mg, 2.00 mmol), cuprous iodide (38 mg, 0.20 mmol) and potassium phosphate tribasic (424 mg, 2.00 mmol) in dimethyl sulfoxide (2.0 mL) were degassed with argon under sonication. The mixture was heated at 100° C. for 5 hours then cooled to ambient temperature. The resultant mixture was diluted with dimethyl sulfoxide (5.0 mL) and ammonium chloride (320 mg, 6.00 mmol) and triethylamine (1.4 mL, 10.0 mmol) were added. To the stirred suspension was then added 1-[bis(dimethylamino)methylene]-1H-1,2,3-triazolo[4,5-b]pyridinium 3-oxide hexafluorophosphate (2.28 g, 6.0 mmol), portion-wise, and the reaction mixture was stirred at room temperature for 10 minutes. The resultant mixture was diluted with 15% aqueous ammonia solution and extracted with ethyl acetate. The combined organic extracts were washed with brine, dried over magnesium sulfate, filtered and evaporated in vacuo. The crude residue was purified via flash chromatography on silica gel (solvent gradient: 0-7% methanol in ethyl acetate). The residue was dissolved in a minimum of acetonitrile. Water was then added to precipitate a solid which was collected by filtration and dried in vacuo to yield 324 mg (75%) of 103 as an off-white solid. LCMS (ESI): R$_T$ (min)=3.21, [M+H]$^+$=434, Method=A; $^1$H NMR (400 MHz, DMSO-d$_6$) δ 7.98 (d, J=8.6 Hz, 1H), 7.40 (br s, 1H), 7.17 (s, 1H), 7.03 (br s, 1H), 6.71 (t, J=56.0 Hz, 1H), 6.42 (dd, J=8.9, 2.4 Hz, 1H), 6.24 (d, J=7.2 Hz, 1H), 6.09 (d, J=2.4 Hz, 1H), 5.01-4.89 (m, 1H), 4.63-4.51 (m, 2H), 4.38-4.29 (m, 4H), 3.15 (t, J=7.7 Hz, 1H), 1.16-1.05 (m, 1H), 0.56-0.44 (m, 3H), 0.33-0.25 (m, 1H).

Example 104 (S)-2-Cyclopropyl-2-((2-((R)-4-methyl-2-oxooxazolidin-3-yl)-5,6-dihydrobenzo[f]imidazo[1,2-d][1,4]oxazepin-9-yl)amino)acetamide 104

A mixture of (R)-3-(9-bromo-5,6-dihydroimidazo[1,2-d][1,4]benzoxazepin-2-yl)-4-methyl-oxazolidin-2-one (Example 102, step 3) (1.098 mmol, 400 mg), cuprous iodide (0.330 mmol, 62.8 mg), (2S)-2-amino-2-cyclopropyl-acetic acid (3.295 mmol, 379.3 mg) and potassium phosphate tribasic (4.393 mmol, 951.5 mg) in dimethyl sulfoxide (35 mmol, 2.5 mL) was heated at 110° C. for 2 hours under microwave irradiation. The reaction was cooled to room temperature. To the reaction mixture was added 1-[bis(dimethylamino)methylene]-1H-1,2,3-triazolo[4,5-b]pyridinium 3-oxide hexafluorophosphate (12.08 mmol, 4260 mg), ammonium chloride (12.08 mmol, 646 mg) and triethylamine (1.53 mL, 11.0 mmol). After 20 minutes at room temperature, the reaction mixture was treated with water then extracted with dichloromethane. The combined organic extracts were washed with brine, dried over magnesium sulfate, filtered and evaporated in vacuo. The crude product was purified via reverse-phase HPLC and lyophilized to yield 110 mg (25% over 2 steps) of 104. LCMS (ESI): $R_T$ (min)=2.588. [M+H]$^+$=398.2, method=B; $^1$H NMR (400 MHz, DMSO-d$_6$) δ 7.96 (d, J=8.8 Hz, 1H), 7.39 (d, J=2.2 Hz, 1H), 7.13 (s, 1H), 7.02 (d, J=2.3 Hz, 1H), 6.42 (dd, J=8.9, 2.4 Hz, 1H), 6.20 (d, J=7.1 Hz, 1H), 6.09 (d, J=2.4 Hz, 1H), 4.61-4.49 (m, 2H), 4.40-4.27 (m, 4H), 4.10-3.99 (m, 1H), 3.22-3.09 (m, 1H), 1.42-1.36 (m, 3H), 1.16-1.04 (m, 1H), 0.56-0.42 (m, 3H), 0.32-0.27 (m, 1H).

Example 105 (S)-2-Cyclopropyl-2-((2-((S)-4-(fluoromethyl)-2-oxooxazolidin-3-yl)-5,6-dihydrobenzo[f]imidazo[1,2-d][1,4]oxazepin-9-yl)amino)acetamide 105

Step 1: (R)-1-(tert-Butyldimethylsilanyloxy)-3-fluoropropan-2-ol

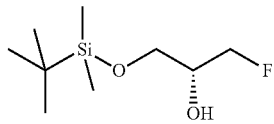

tert-Butyldimethylsilyl chloride (1.60 g, 10.63 mmol) was added to a solution of (R)-3-fluoropropane-1,2-diol (1.00 g, 10.6 mmol), triethylamine (1.93 mL, 13.8 mmol) and catalytic 4-(dimethylamino)pyridine in dichloromethane at 0° C. and the reaction mixture was allowed to warm to room temperature and stirred at room temperature for 16 hours. The reaction mixture was diluted with water and extracted with dichloromethane. The combined organic fractions were washed with brine, dried over magnesium sulfate, filtered and evaporated in vacuo. The resultant crude residue was purified via flash chromatography on silica gel (solvent gradient: 0-40% ethyl acetate in cyclohexane) to yield 1.80 g (81%) of the title compound as a colorless oil. $^1$H NMR (400 MHz, CDCl$_3$) δ 4.45-4.36 (m, 1H), 4.34-4.25 (m, 1H), 3.87-3.73 (m, 1H), 3.66-3.56 (m, 2H), 2.30 (d, J=6.0 Hz 1H), 0.82 (s, 9H), 0.00 (s, 6H).

Step 2: (S)-2-Azido-3-fluoropropoxy)-tert-butyldimethylsilane

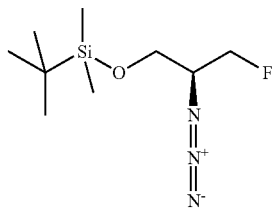

Trifluoromethanesulfonic anhydride (1.67 mL, 9.93 mmol) was added dropwise to a solution of (R)-1-(tert-butyldimethylsilanyloxy)-3-fluoropropan-2-ol (1.80 g, 8.60 mmol) and pyridine (1.2 mL, 13.8 mmol) in dichloromethane at −20° C. and the reaction mixture stirred at −20° C. for 20 minutes then at 0° C. for 30 minutes. The reaction mixture was diluted with 0.5 N aqueous HCl and extracted with dichloromethane. The combined organic extracts were dried over magnesium sulfate, filtered and evaporated in vacuo. The residue was dissolved in N,N-dimethylformamide (5.0 mL) and sodium azide (1.68 g, 25.9 mmol) was added. The reaction mixture was stirred at room temperature for 2 hours. The resultant mixture was diluted with water and extracted with ethyl acetate. The combined organic extracts were washed with brine, dried over magnesium sulfate, filtered and evaporated in vacuo to yield the crude title compound which was carried forward without purification. $^1$H NMR (400 MHz, CDCl$_3$) δ 4.58-4.26 (m, 2H), 3.75-3.63 (m, 2H), 3.62-3.46 (m, 1H), 0.80 (s, 9H), 0.00 (s, 6H).

Step 3: (S)-1-(tert-Butyldimethylsilanyloxymethyl)-2-fluoroethylamine

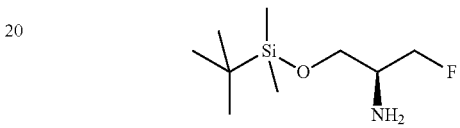

Palladium hydroxide (400 mg, 20% on carbon) was added to a solution of ((S)-2-azido-3-fluoropropoxy)-tert-butyldimethylsilane (crude, assume 8.60 mmol) in ethyl acetate (15 mL) and methanol (5.0 mL) and the reaction mixture was stirred under a balloon of hydrogen for 16 hours. The resultant mixture was filtered, fresh palladium hydroxide (400 mg, 20% on carbon) was added and the reaction was stirred under a balloon of hydrogen for a further 16 hours. The resultant mixture was filtered and the filtrate was evaporated in vacuo to yield the title compound as a ~2:1 mixture of product:starting material, which was carried forward without purification.

Step 4: (S)-4-Fluoromethyloxazolidin-2-one

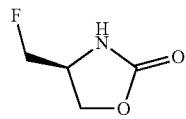

HCl in dioxane (4 N, 2.0 mL, 8.00 mmol) was added to a solution of (S)-1-(tert-butyldimethylsilanyloxymethyl)-2-fluoroethylamine (crude, assume 8.60 mmol) in methanol (3.0 mL) and the resulting mixture was stirred at room temperature for 2 hours. The reaction mixture was evaporated in vacuo. The resultant residue was dissolved in a mixture of toluene (20 mL) and KOH (2.89 g, 51.6 mmol, 12.5% aq) at 0° C. To this mixture was added, dropwise, phosgene (13.6 mL, 20% in toluene), the cooling bath was removed and the resultant mixture was stirred for 1 hour. The reaction mixture was evaporated in vacuo and the resultant residue was extracted with hot industrial methylated spirits. The filtrate was evaporated in vacuo and the resultant residue was purified via flash chromatography on silica gel (solvent gradient: 50-100% ethyl acetate in cyclohexane) to yield 450 mg (44%, 3 steps) of the title compound as an off-white solid. $^1$H NMR (400 MHz, CDCl$_3$) δ 5.69 (br s, 1H), 4.59-4.42 (m, 2H), 4.42-4.32 (m, 1H), 4.25-4.08 (m, 2H).

Step 5: (S)-3-(9-Bromo-5,6-dihydrobenzo[f]imidazo[1,2-d][1,4]oxazepin-2-yl)-4-(fluoromethyl)oxazolidin-2-one and (S)-3-(9-Iodo-5,6-dihydrobenzo[f]imidazo[1,2-d][1,4]oxazepin-2-yl)-4-(fluoromethyl)oxazolidin-2-one

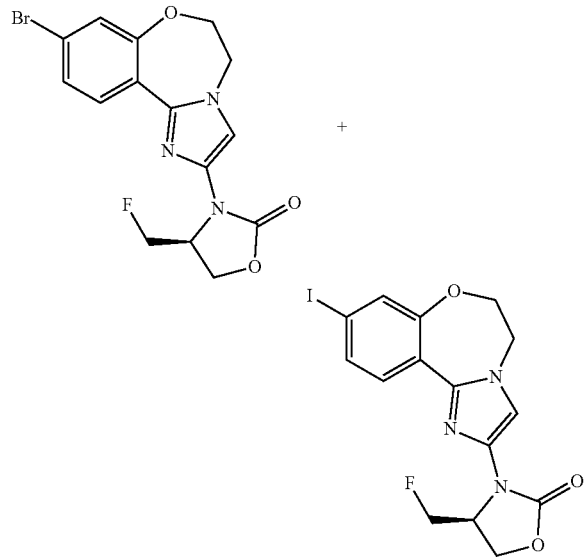

A mixture of 9-bromo-2-iodo-5,6-dihydrobenzo[f]imidazo[1,2-d][1,4]oxazepine (722 mg, 1.85 mmol), (S)-4-fluoromethyloxazolidin-2-one (220 mg, 1.85 mmol), 3,4,7,8-tetramethyl-1,10-phenanthroline (131 mg, 0.55 mmol), Cu(OAc)$_2$.H$_2$O (74 mg, 0.37 mmol), potassium carbonate (510 mg, 3.70 mmol) and dioxane (6.0 ml) were sealed in a tube and the mixture degassed with argon under sonication. The reaction mixture was heated at 100° C. for 72 hours. The resultant reaction mixture was diluted with 15% aqueous ammonia and extracted with ethyl acetate. The combined organic extracts were washed with brine, dried over magnesium sulfate, filtered and evaporated in vacuo. The crude residue was purified via flash chromatography on silica gel (solvent gradient: 0-100% ethyl acetate in cyclohexane) to yield 390 mg (53%) of the title compounds (approximate 2:1 mixture of 9-Br and 9-I products). LCMS (ESI): [M+H]$^+$=382/384/430; $^1$H NMR (400 MHz, CDCl$_3$) δ 8.22 (d, J=9.3 Hz, 0.7H), 8.05 (d, J=8.8 Hz, 0.3H), 7.43-7.37 (m, 0.6H), 7.29 (s, 1.2H), 7.23-7.18 (m, 1.2H), 5.03-4.66 (m, 3H), 4.60 (t, J=8.5 Hz, 1H), 4.54 (dd, J=8.6, 4.3 Hz, 1H), 4.47-4.43 (m, 2H), 4.37-4.33 (m, 2H).

Step 6: (S)-2-Cyclopropyl-2-((2-((S)-4-(fluoromethyl)-2-oxooxazolidin-3-yl)-5,6-dihydrobenzo[f]imidazo[1,2-d][1,4]oxazepin-9-yl)amino)acetamide A mixture of (S)-3-(9-bromo-5,6-dihydrobenzo[f]imidazo[1,2-d][1,4]oxazepin-2-yl)-4-(fluoromethyl)oxazolidin-2-one and (S)-3-(9-iodo-5,6-dihydrobenzo[f]imidazo[1,2-d][1,4]oxazepin-2-yl)-4-(fluoromethyl)oxazolidin-2-one (195 mg, ~2:1 mix Br:I, ~0.49 mmol), L-cyclopropylglycine (104 mg, 0.90 mmol), cuprous iodide (17 mg, 0.09 mmol) and potassium phosphate tribasic (190 mg, 0.90 mmol) in dimethyl sulfoxide (1.5 mL) was degassed with argon under sonication. The reaction mixture was heated at 100° C. for 16 hours then cooled to room temperature. The resultant mixture was diluted with dimethyl sulfoxide (1.0 mL) and ammonium chloride (144 mg, 2.70 mmol) and triethylamine (950 µL, 6.75 mmol) were added. To this mixture was then added 1-[bis(dimethylamino)methylene]-1H-1,2,3-triazolo[4,5-b]pyridinium 3-oxide hexafluorophosphate (1.54 g, 4.05 mmol), portion-wise, and the reaction mixture was stirred at room temperature for 1 hour. The resultant mixture was diluted with saturated aqueous sodium bicarbonate solution and extracted with ethyl acetate. The combined organic extracts were washed with brine, dried over magnesium sulfate, filtered and evaporated in vacuo. The resultant crude residue was purified via flash chromatography on silica gel (solvent gradient: 0-5% methanol in dichloromethane) and then further purified by flash chromatography on silica gel (solvent gradient: 0-100% methyl acetate in cyclohexane) to yield 90 mg (48%) of 105 as an off-white solid. LCMS (ESI): R$_T$ (min)=2.76 [M+H]$^+$=416, Method=A; $^1$H NMR (400 MHz, DMSO-d$_6$) δ 7.94 (d, J=8.8 Hz, 1H), 7.40 (br s, 1H), 7.17 (s, 1H), 7.03 (br s, 1H), 6.41 (dd, J=8.8, 2.3 Hz, 1H), 6.22 (d, J=7.1 Hz, 1H), 6.09 (d, J=2.2 Hz, 1H), 4.99 (ddd, J=48.3, 9.8, 2.5 Hz, 1H), 4.81-4.56 (m, 3H), 4.40 (dd, J=8.6, 3.9 Hz, 1H), 4.37-4.29 (m, 4H), 3.15 (t, J=7.6 Hz, 1H), 1.16-1.05 (m, 1H), 0.54-0.43 (m, 3H), 0.33-0.25 (m, 1H).

Example 106 (S)-2-((2-((S)-4-(Fluoromethyl)-2-oxooxazolidin-3-yl)-5,6-dihydrobenzo[f]imidazo[1,2-d][1,4]oxazepin-9-yl)amino)propanamide 106

A mixture of (S)-3-(9-bromo-5,6-dihydrobenzo[f]imidazo[1,2-d][1,4]oxazepin-2-yl)-4-(fluoromethyl)oxazolidin-2-one and (S)-3-(9-iodo-5,6-dihydrobenzo[f]imidazo[1,2-d][1,4]oxazepin-2-yl)-4-(fluoromethyl)oxazolidin-2-one (Example 105, step 5) (195 mg, approximate 2:1 mixture 9-Br:9-I, approximate 0.49 mmol), L-alanine (87 mg, 0.98 mmol), cuprous iodide (17 mg, 0.09 mmol) and potassium phosphate tribasic (208 mg, 0.98 mmol) in dimethyl sulfoxide (3.0 mL) were degassed with argon under sonication. The reaction mixture was heated at 100° C. for 4 hours then cooled to room temperature. The resultant mixture was diluted with dimethyl sulfoxide (3.0 mL) and ammonium chloride (157 mg, 2.94 mmol) and triethylamine (683 µL, 4.8 mmol) were added. To this mixture was then added 1-[bis(dimethylamino)methylene]-1H-1,2,3-triazolo[4,5-b]pyridinium 3-oxide hexafluorophosphate (1.10 g, 2.94 mmol), portion-wise, and the reaction mixture was stirred at room temperature for 30 minutes. The resultant mixture was diluted with saturated aqueous sodium bicarbonate solution and extracted with ethyl acetate. The combined organic extracts were washed with brine, dried over magnesium sulfate, filtered and evaporated in vacuo. The resultant residue was purified via flash chromatography on silica gel (solvent gradient: 0-5% methanol in dichloromethane) and then further purified by chiral supercritical fluid chromatography to yield 36 mg (19%) of 106 as an off-white solid. LCMS (ESI): R$_T$ (min)=2.43 [M+H]$^+$=390, Method=A; $^1$H NMR (400 MHz, DMSO-d$_6$) δ 7.96 (d, J=8.8 Hz, 1H), 7.37 (br s, 1H), 7.17 (s, 1H), 7.00 (br s, 1H), 6.39 (dd, J=8.6, 1.6 Hz, 1H), 6.15 (d, J=7.0 Hz, 1H), 6.09 (d, J=1.6 Hz, 1H), 5.08-4.55 (m, 5H), 4.42-4.28 (m, 4H), 3.76 (quintet, J=7.2 Hz, 1H), 1.30 (d, J=7.2 Hz, 3H).

Example 107 (S)-2-((2-((S)-4-(Difluoromethyl)-2-oxooxazolidin-3-yl)-5,6-dihydrobenzo[f]imidazo[1,2-d][1,4]oxazepin-9-yl)amino)butanamide 107

A mixture (S)-3-(9-bromo-5,6-dihydrobenzo[f]imidazo[1,2-d][1,4]oxazepin-2-yl)-4-(difluoromethyl)oxazolidin-2- one (Example 101, step 12) (240 mg, 0.60 mmol), (S)-2-aminobutyric acid (124 mg, 1.19 mmol), cuprous iodide (22.8 mg, 0.119 mmol), potassium phosphate tribasic (255 mg, 1.19 mmol) and dimethyl sulfoxide (6.0 mL) was stirred under argon at 100° C. for 6 hours. The resultant mixture was allowed to cool to room temperature and then ammonium chloride (188 mg, 3.52 mmol) and triethylamine (1.2 mL, 8.80 mmol) were added. To the stirred suspension was added 1-[bis(dimethylamino)methylene]-1H-1,2,3-triazolo[4,5-b]pyridinium 3-oxide hexafluorophosphate (2.01 g, 5.28 mmol), portion-wise, and the reaction mixture was stirred at room temperature for 1 hour. The resultant mixture was diluted with ethyl acetate, washed with saturated ammonium chloride, dried over magnesium sulfate, filtered, and evaporated in vacuo. The crude product was purified via flash chromatography on silica gel (solvent gradient: 0-10% methanol in ethyl acetate), further purified via reverse-phase HPLC, then chiral supercritical fluid chromatography to yield 73.6 mg (30%) of 107 as a white solid. LCMS (ESI): $R_T$ (min)=3.13, [M+H]$^+$=422, Method=A; $^1$H NMR (400 MHz, DMSO-$d_6$) δ 7.99 (d, J=8.8 Hz, 1H), 7.40 (s, 1H), 7.17 (s, 1H), 7.03 (s, 1H), 6.71 (t, J=56.0 Hz, 1H), 6.44 (dd, J=8.8, 2.2 Hz, 1H), 6.13 (d, J=2.2 Hz, 1H), 6.09 (d, J=7.6 Hz, 1H), 5.02-4.89 (m, 1H), 4.62-4.53 (m, 2H), 4.41-4.27 (m, 4H), 3.65-3.60 (m, 1H), 1.72-1.59 (m, 2H), 0.94 (t, J=7.3 Hz, 3H).

Example 901 p110α (Alpha) PI3K Binding Assay

PI3K Binding assays are intended for determining the biochemical potency of small molecule PI3K inhibitors. The PI3K lipid kinase reaction is performed in the presence of PIP2:3PS lipid substrate (Promega #V1792) and ATP. Following the termination if the kinase reaction, turnover of ATP to ADP by the phosphorylation of the lipid substrate is detected using the Promega ADP-Glo™ (Promega #V1792) assay. Reactions are carried out using the following conditions for each PI3K isoform as in Table 5.

TABLE 5

| Kinase | Source | Final Kinase Concentration | ATP (uM) | PIP2:3PS (uM) | Reaction Time (min.) |
|---|---|---|---|---|---|
| PI3K alpha | Millipore #14-602-K | 0.2 nM | 40 | 50 | 120 |
| PI3K beta | Promega #V1751 | 0.6 nM | 40 | 50 | 120 |
| PI3K delta | Millipore #14-604-K | 0.25 nM | 40 | 50 | 120 |
| PI3K gamma | Millipore #14-558-K | 0.4 nM | 25 | 50 | 120 |

After 120 minutes of reaction time, the kinase reaction is terminated. Any ATP remaining after the reaction is depleted, leaving only ADP. Then the Kinase Detection Reagent is added to convert ADP to ATP, which is used in a coupled luciferin/luciferase reaction. The luminescent output is measured and is correlated with kinase activity.

All reactions are carried out at room temperature. For each PI3K isoform a 3 μl mixture (1:1) of enzyme/lipid substrate solution is added to a 384 well white assay plate (Perkin Elmer #6007299) containing 50 μl of test compound or DMSO only for untreated to controls. The reaction is started by the addition of 2 μl ATP/MgCl$_2$. The kinase reaction buffer contains 50 mM HEPES, 50 mM NaCl 3 mM MgCl$_2$, 0.01% BSA, 1% DMSO, and enzyme and substrate concentrations as indicated in the above table. The reaction is stopped by the addition of 10 μL ADP-Glo reagent. Plates are read in a Perkin Elmer Envision system using luminescence mode. 10 point dose response curves are generated for each test compound. Ki values for each compound are determined using the Morrison Equation.

Binding Assays: Initial polarization experiments were performed on an Analyst HT 96-384 (Molecular Devices Corp, Sunnyvale, Calif.). Samples for fluorescence polarization affinity measurements were prepared by addition of 1:3 serial dilutions of p110alpha PI3K (Upstate Cell Signaling Solutions, Charlottesville, Va.) starting at a final concentration of 20 ug/mL in polarization buffer (10 mM Tris pH 7.5, 50 mM NaCl, 4 mM MgCl$_2$. 0.05% Chaps. and 1 mM DTT) to 10 mM PIP$_2$ (Echelon-Inc., Salt Lake City, Utah) final concentration. After an incubation time of 30 minutes at room temperature, the reactions were stopped by the addition of GRP-1 and PIP3-TAMRA probe (Echelon-Inc., Salt Lake City, Utah) 100 nM and 5 nM final concentrations respectively. Read with standard cut-off filters for the rhodamine fluorophore (λex=530 nm; λem=590 nm) in 384-well black low volume Proxiplates® (PerkinElmer, Wellesley, Mass.) Fluorescence polarization values were plotted as a function of the protein concentration. EC$_{50}$ values were obtained by fitting the data to a four-parameter equation using KaleidaGraph, software (Synergy software, Reading, Pa.). This experiment also establishes the appropriate protein concentration to use in subsequent competition experiments with inhibitors.

Inhibitor IC$_{50}$ values were determined by addition of the 0.04 mg/mL p110alpha PI3K (final concentration) combined with PIP$_2$ (10 mM final concentration) to wells containing 1:3 serial dilutions of the antagonists in a final concentration of 25 mM ATP (Cell Signaling Technology, Inc., Danvers, Mass.) in the polarization buffer. After an incubation time of 30 minutes at room temperature, the reactions were stopped by the addition of GRP-1 and PIP3-TAMRA probe (Echelon-Inc., Salt Lake City, Utah) 100 nM and 5 nM final concentrations respectively. Read with standard cut-off filters for the rhodamine fluorophore (λex=530 nm; λem=590 nm) in 384-well black low volume Proxiplates® (PerkinElmer, Wellesley, Mass.) Fluorescence polarization values were plotted as a function of the antagonist concentration, and the IC$_{50}$ values were obtained by fitting the data to a 4-parameter equation in Assay Explorer software (MDL, San Ramon, Calif.).

Alternatively, inhibition of PI3K was determined in a radiometric assay using purified, recombinant enzyme and ATP at a concentration of 1 μM (micromolar). The compound was serially diluted in 100% DMSO. The kinase reaction was incubated for 1 h at room temperature, and the reaction was terminated by the addition of PBS. IC$_5$ values were subsequently determined using sigmoidal dose-response curve fit (variable slope).

Example 902 Selective Inhibition of Mutant PI3Kα (Alpha)

The ability of a compound of the invention to act preferentially against cells containing mutant PI3Kα (alpha) was determined by measuring inhibition of the PI3K pathway in SW48 isogenic cell lines: PI3Kα wild-type (parental), helical domain mutant E545K, and kinase domain mutant H1047R. The following assays are intended for determining the cellular potency and mutant selectivity of small molecule PI3Kα inhibitors. The assay utilizes isogenic cell lines that express PI3Kα WT, PI3Kα mutant E545K+ (Horizon Discovery 103-001), or PI3Kα mutant H1047R/+ (Horizon Discovery 103-005). The potency of pPRAS40 inhibition by PI3Kα in each cell line is measured after 24 hours of compound treatment. Mutant selectivity of PI3Kα inhibitors is determined by $EC_{50}$ potency ratios in the WT vs. E545K cell lines and WT vs. H1047R cell lines.

Cell Culture: Cell lines are maintained in a cell culture incubator at 37° C. and 5% $CO_2$ in cell culture medium containing RPMI1640 (prepared at Genentech), 10% FBS (Gibco 16140-071), 2 mM L-glutamine (prepared at Genentech), and 10 mM HEPES pH 7.2 (prepared at Genentech). Cells are split every 72 hours at a ratio of 1:8 using 0.25% Trypsin-EDTA (Gibco 25200).

Assay Procedure: Cells are harvested and plated in 384 well tissue culture treated assay plates (Greiner cat #781091) and incubated overnight at 37° C. at 5% $CO_2$. The three cell lines (WT, E545K, and H1047R) are plated and assayed in parallel. The following day, test compounds are serially diluted in dimethyl sulfoxide (DMSO) and added to cells (final DMSO concentration 0.5%). Cells are then incubated for 24 hours at 37° C. and 5% $CO_2$. After 24 hours, cells are lysed and pPRAS40 levels are measured using the Meso-Scale custom pPRAS40 384w Assay Kit (Meso Scale Discovery., cat # L21CA-1). Cell lysates are added to assay plates pre-coated with antibodies against phosphorylated PRAS40. Phosphorylated PRAS40 in samples are allowed to bind to the capture antibodies overnight at 4° C. The detection antibody (anti-total PRAS40, labeled with an electrochemiluminescent SULFO-TAG) is added to the bound lysate and incubated for 1 hour at room temperature. The MSD Read Buffer is added such that when a voltage is applied to the plate electrodes, the labels bound to the electrode surface emit light. The MSD Sector Instrument measures the intensity of the light, and quantitatively measures the amount of phosphor-PRAS40 in the sample. Percent inhibition of PRAS40 phosphorylation by varying concentrations of test compounds is calculated relative to untreated controls. $EC_{50}$ values are calculated using the 4 parameter logistic nonlinear regression dose-response model.

Statistical Analysis: $EC_{50}$ values represent the geometric mean of a minimum of 4 independent experiments. All statistics were performed using KaleidaGraph Software (version 4.1.3). A Student t-Test was performed using unpaired data with equal variance to compare activity against mutant cells and wild-type cells. $P<0.05$ is considered to be significant.

Example 903 In Vitro Cell Viability Assays

Cells were seeded (1,500 per well) in 384-well plates for 16 h. On day 2, nine serial 1:3 compound dilutions were made in DMSO in a 96-well plate. The compounds were then further diluted into growth media using a Rapidplate robot (Zymark Corp.). The diluted compounds were then added to quadruplicate wells in the 384-well cell plates and incubated at 37° C. and 5% $CO_2$. After 4 d, relative numbers of viable cells were measured by luminescence using Cell Titer-Glo (Promega) according to the manufacturer's instructions and read on a Wallac Multilabel Reader (Perkin-Elmer). EC50 values were calculated using Prism 6.0 software (GraphPad).

Example 904 In Vivo Mouse Tumor Xenograft Efficacy

Mice:
Female severe combined immunodeficiency mice (C.B-17 SCID.bg Charles River Labs, San Diego), NOD.SCID (Charles River Labs, Hollister) or NCR.nude mice (Taconic) were 8 to 9 weeks old and had a BW range of 18-26 grams on Day 0 of the study. The animals received ad libitum water and Laboratory Autoclavable Rodent Diet 5010 (LabDiet St. Louis, Mo.). The mice were housed in microisolators on a 12-hour light cycle. Genentech specifically complies with the recommendations of the Guide for Care and Use of Laboratory Animals with respect to restraint, husbandry, surgical procedures, feed and fluid regulation, and veterinary care. The animal care and use program at Genentech is accredited by the Association for Assessment and Accreditation of Laboratory Animal Care International (AAALAC), which ensures compliance with accepted standards for the care and use of laboratory animals. The mice were housed at Genentech in standard rodent micro-isolator cages and were acclimated to study conditions for at least 3 days before tumor cell implantation. Only animals that appeared to be healthy and that were free of obvious abnormalities were used for the study Tumor Implantation:
Xenografts were initiated with either cancer cells (HCC1954x1 or KPL4) or passage tumors (HCl-003). Cells were cultured in RPMI 1640 medium supplemented with 10% fetal bovine serum, 2 mM glutamine, 100 units/mL penicillin, 100 µg/mL (micrograms per ml) streptomycin sulfate and 25 µg/mL gentamicin, harvested in the log-phase growth and resuspended in 50% phenol red-free Matrigel (Becton Dickinson Bioscience; San Jose, Calif.) and Hank's Balanced Salt Solution at a concentration of 3×106 or 5×106 cells/mL depending on the doubling time of the cell line. For the HCl-003 patient-derived model, 30 mg beeswax pellets containing approximately 1 mg of 17/J (beta)-estradiol were implanted subcutaneously 3 days prior to implantation of tumor fragments. Tumor cells or fragments were implanted into the 2/3 mammary fat pad, and tumor growth was monitored as the average size approached the target range of 100 to 250 mm3. Once the majority of tumors reached the target range, Mice were distributed into groups of 7-10 mice based on tumor volume.

Therapeutic Agents:
PI3K compounds were supplied as a free base in dry powder and stored at room temperature protected from light. The vehicle for taselisib (GDC-0032) and BYL719 was 0.5% methylcellulose: 0.2% Tween 80 (MCT) in deionized water. The vehicle control for compound 101 was 0.5% methylcellulose/0.2% Tween-80 (MCT) nanosuspension. MCT nanosuspension is prepared by initially preparing a MCT suspension. Once prepared, 1 mm glass beads and a rare earth magnetic stir bar are used to mill the MCT suspension for about 24 hours into a fine nanosuspension. Particle size analyzer was used to check final particle size. Drug doses were prepared weekly and stored at 4 C.

Treatment:
Mice were given (Vehicle) or stated mg/kg dosage of PI3K compounds (expressed as free-base equivalent), PO by gavage daily for 21-28 days in a volume of 100 µL, microliters (5 mL/kg).

Endpoint:
Tumor volume was measured in 2 dimensions (length and width), using Ultra Cal IV calipers (Model 54 10 111; Fred V. Fowler Company), as follows: tumor volume $(mm^3)=$ (length×width$^2$)×0.5 and analyzed using Excel version 11.2 (Microsoft Corporation). A linear mixed effect (LME) modeling approach was used to analyze the repeated measurement of tumor volumes from the same animals over time (Pinheiro J, et al. nlme: linear and nonlinear mixed effects models, 2009; R package version 3.2.5. This approach addresses both repeated measurements and modest dropouts due to any non-treatment-related death of animals before study end. Cubic regression splines were used to fit a nonlinear profile to the time courses of log 2 tumor volume at each dose level. These nonlinear profiles were then related to dose within the mixed model. Tumor growth inhibition as a percentage of vehicle control (% TGI) was calculated as the percentage of the area under the fitted curve (AUC) for the respective dose group per day in relation to the vehicle, using the following formula % TGI=100×(1−AUC$_{dose}$/AUC$_{veh}$). Using this formula, a TGI value of 100% indicates tumor stasis, a TGI value of more than (>) 1% but less than (<) 100% indicates tumor growth delay, and a TGI value of more than (>) 100% indicates tumor regression. Partial response (PR) for an animal was defined as a tumor regression of more than (>) 50% but less than (<) 100% of the starting tumor volume. Complete response (CR) was defined as 100% tumor regression (i.e., no measurable tumor) on any day during the study.

Toxicity:

Animals were weighed daily for the first five days of the study and twice weekly thereafter. Animal body weights were measured using an Adventurer Pro® AV812 scale (Ohaus Corporation). Percent weight change was calculated as follows: body weight change (%)=[(weight$_{day\ new}$−weight$_{day\ 0}$)/weight$_{day\ 0}$]×100. The mice were observed frequently for overt signs of any adverse, treatment-related side effects, and clinical signs of toxicity were recorded when observed. Acceptable toxicity is defined as a group mean body weight (BW) loss of less than 20% during the study and not more than one treatment-related (TR) death among ten treated animals. Any dosing regimen that results in greater toxicity is considered above the maximum tolerated dose (MTD). A death is classified as TR if attributable to treatment side effects as evidenced by clinical signs and/or necropsy, or may also be classified as TR if due to unknown causes during the dosing period or within 10 days of the last dose. A death is classified as NTR if there is no evidence that death was related to treatment side effects.

Example 905. Cell Culture and In Vitro Inhibitor Experiments

Cell lines were grown under standard tissue culture conditions in RPMI media with 10% fetal bovine serum, 100 U/mL penicillin, and 100 µg/mL streptomycin. HCC-1954 and HDQ-P1 are breast cancer cell lines (American Type Culture Collection; Manassas, Va. HCC-1954 and HDQ-P1 cells were placed in each well of a 6-well tissue culture plate at 800,00 cells/well and incubated at 37° C. overnight. Cells were incubated with the indicated concentrations of each compound for 24 hours. Following incubation, cells were washed once with cold phosphate-buffered saline (PBS) and lysed in Biosource™ Cell Extraction Buffer (Invitrogen; Carlsbad, Calif.) supplemented with protease inhibitors (F. Hoffman-LaRoche; Mannheim, Germany), 1 mM phenylmethylsulfonyl fluoride, and Phosphatase Inhibitor Cocktails 1 and 2 (Sigma-Aldrich; St. Louis, Mo.). Protein concentrations were determined using the Pierce BCA Protein Assay Kit (Thermo Fisher Scientific; Rockford, Ill.).

Protein Assays

Protein concentration was determined using the Pierce BCA Protein Assay Kit (Rockford, Ill.). For immunoblots, equal protein amounts were separated by electrophoresis through NuPage Bis-Tris 4-12% gradient gels (Invitrogen; Carlsbad, Calif.); proteins were transferred onto Nitrocellulose membranes using the IBlot system and protocol from InVitrogen. Antibodies to p110alpha, and phospho-Akt (Ser473), were obtained from Cell Signaling (Danvers, Mass.). Antibodies to O-actin and GAPDH were from Sigma.

Example 906 B-Cell CD69 Expression, Human Whole Blood Assay for CD69 Expression in CD19$^+$ CD27$^-$ B Cells Cell Culture:

Human whole blood was dispensed into 96-deep well plates at 100 µl per well. Compounds were diluted in DMSO to generate the desired stock concentrations and then further diluted in PBS to the desired working concentration and added in a volume of 5.5 µL per well. Samples were then incubated for 1 hour at 37° C. under 5% CO$_2$ before the addition of 5 µg (10 µl per well) of Goat anti IgM F(ab')2 (Southern Biotech, AL), and incubated for 18 hours at 37° C. under 5% CO$_2$. All treatments were tested in duplicate.

Cell Isolation and Staining Procedures:

After incubation, the level of CD69 expression on CD19$^+$ CD27$^-$ cells was determined by staining the whole blood samples with a cocktail of CD27; 10 µl/well (clone L128; BD Biosciences, NJ) CD19; 7.5 µl/well (clone SJ25C1; BD Biosciences, NJ) and CD69; 10 µl (clone FN50; BD Biosciences, NJ). In addition, human whole blood from each donor was stained with isotype-matched fluorescent control antibodies. After the addition of the appropriate antibody cocktail the whole blood samples were stained for 30 minutes in the dark and then lysed using BD Pharm Lysis (BD Bioscience, NJ). The resulting samples were then washed with FACS Buffer (Phosphate Buffered Saline (Ca: Mg++ free), 1 mM EDTA, 25 mM HEPES pH 7.0, 1% Fetal Bovine Serum (Heat-Inactivated) and fixed in FACS Buffer supplemented with 0.1% Formaldehyde (Polysciences Inc, PA) and 0.1% Pluronic F-68 (Sigma, MO). Data were acquired using a BD LSR-II (BD Biosciences) with BD FACSDiva software.

CD69 Expression of CD19$^+$ CD27$^-$ B Cells.

Cells were assessed by flow cytometry for levels of CD19, CD27 and CD69 using BD FACSDiva Software and the CD69 MFI-Mean of the CD19$^+$ CD27$^-$ lymphocyte population was determined. The concentration of compound resulting in 50% inhibition of CD69 MFI-Mean (IC$_{50}$) was determined using Genedata software (Genedata Screener, MA).

Example 907 HCC1954 and HDQP1 pPRAS40 EC$_{50}$

Cells are plated in 384 well tissue culture treated assay plates and incubated overnight. The following day, cells are treated with compounds and incubated for 24 hours. After 24 hours, cells are lysed and pPRAS40 levels are measured using the Meso-Scale assay platform. These cell lines are quite useful for characterizing the selectivity of PI3Kα inhibitors for mutant PI3Kα. The HCC1954 cell line expresses mutant PI3Kα (E545K) vs WT in HDQP1.

Assay Principle:

The MSD platform provides a method of measuring the phosphorylated levels of pPRAS40 in a single sample. Cell lysates are added to assay plates pre-coated with antibodies against total PRAS40. Following cell lysis, PRAS40 in samples is allowed to bind to the capture antibodies. The detection antibody (anti-phospho PRAS40), labeled with an electrochemiluminescent compound MSD SULFO-TAG, is added to the bound lysate. The MSD Read Buffer is added such that when a voltage is applied to the plate electrodes, the labels bound to the electrode surface emit light. The MSD Sector Instrument measures the intensity of the light, and quantitatively measures the amount of phosphor_EGFR in the sample (Meso Scale Assay Principle).

Materials:

| | |
|---|---|
| Assay plate | Black u-Clear bottom 384 well sterile, TC treated plates (Greiner cat # 781091) |
| Cell Types | WT Parental Line: HDQ-P1 (CL131963) E545K Mutant: HCC1954 (CL130216) |
| Media | RPMI 1640 10% FBS (Gibco 16140-071) 2 mM L-Glutamine (GNE in-house) 1% HEPES (GNE in-house) |
| Other cell culture reagents | 0.25% Trypsin EDTA 1X (Invitrogen Gibco, cat # 25200) |
| Assay reagent kit | Whole Cell Lysate Kit custom pPRAS40 384w Assay Kit (Meso Scale Discovery, cat # L21CA-1 for 100 plates) |

Procedure:

Compounds prepared at concentration of 2 mM in DMSO. Prepare DMSO compound titration plate, 1:3 in neat DMSO.

DMSO Mother plate contains 72 µl of 13 compounds.

Mutant selective control compound: Add 72 ul of 2 mM control compound to well B2 on each assay plate. This control compound demonstrates approximately 20 fold greater potency in the HCC1954 cell line vs. the HDQP1 line.

Using a multi-channel pipette, transfer 36 ul from each compound well to the well directly below (example B2 to C2) in order to set up duplicate dose-response curves.

Use Biomek Fx method titled "SLS_serial dilution/1 plate_384_3_13_3x" to make serial dilutions of compounds in mother plate.

Seal and keep both the DMSO Mother and Daughter plates with a heat sealer when not in use.

Day 1: Cell Plating
1. Seed 12.500 cells in 45 ul medium for each cell line. Allow cells to settle/attach to plate for 15-20 min at room temperature.
2. Incubate cells overnight in a 37° C. humidity and CO2 controlled incubator.

Day 2: Compound Plate Preparation and Compound Treatment
1. For the 10× intermediate dilution plate: add 95 ul serum-free media into a standard profile greiner 384 well polypropylene plate.
2. Use biomek Fx protocol for intermediate compound dilution in media and addition to cells: "SLS Intermed Dil Add 5 ul to Cells Jul. 13, 2012." This Biomek protocol transfers 5 ul from the DMSO daughter plate to the intermediate dilution plate containing 95 ul medium and mixes the media+compounds. The method then transfers 5 ul from the intermediate dilution plate to the appropriate cell plate.
3. Incubate the treated cells at 37 degrees for 24 hours in a 5% CO2 humidified incubator.

Day 3: Cell Lysis and Addition to MSD Plates

Block the MSD assay plate with 50 ul 3% Blocker A/1×MSD Wash Buffer 1-2 hr at room temp. This solution can be stored at 4° C. for up to one month. Blocking buffer A contains 1×MSD wash buffer. 20 mL 1× Tris Wash buffer and 600 mg Blocker A.

Prepare Lysis Buffer:

| | 3 plates (mL) | 6 plates (mL) | 9 plates (mL) | 12 plates (mL) |
|---|---|---|---|---|
| MSD Lysis Buffer | 65.0 | 120 | 180 | 240 |
| Phosphatase Inh. Cocktail 1 (or Sigma phosphatase Inhib 2 Cat# P5726-5 mL) | 0.65 | 1.2 | 1.8 | 2.4 |
| Phosphatase Inh. Cocktail 2 (or Sigma phosphatase Inhib 3, Cat# P0044-5 mL) | 0.65 | 1.2 | 1.8 | 2.4 |
| Protease inh (or Sigma Cat# P2714-1BTL resuspended in 10 mL PBS) | 0.65 | 1.2 | 1.8 | 2.4 |

Aspirate Media and Lyse the Cells
1. Lyse the cells in 50 µl lysis buffer. Lyse at room temperature for 10-20 minutes on plate shaker.
2. While cells are lysing, wash blocked plates 1×MSD wash buffer.
3. Transfer 42 ul lysates (21+21 µL) to a blocked MSD pPRAS40 assay plate.
4. Seal MSD plates and incubate at 4° C. with shaking overnight.

Day 4: MSD Assay/Detection
8. Make a solution of 1% Blocker A in 1×MSD wash buffer. (20 mL 1× Tris Wash buffer and 200 mg Blocker A (1% w/v). This solution can be stored at 4° C. for up to one month.
9. Wash the MSD plates with 1×MSD wash buffer.
10. Add 10 µl of the diluted SULFO-TAG detection antibody to the plates. Incubate for 1 hr with shaking at room temp.

| | 3 plates (mL) | 6 plates (mL) | 9 plates (mL) | 12 plates (mL) |
|---|---|---|---|---|
| 1% blocker A in MSD wash buffer | 13.0 | 25.0 | 36.0 | 48.0 |
| 2% blocker DM (100X) | 0.13 | 0.25 | 0.36 | 0.48 |
| Sulfo-TAG anti-pPRAS40 (50X) | 0.26 | 0.5 | 0.72 | 0.96 |

11. Wash the plates 4× with 1×MSD wash buffer.
12. Add 35 µl 1× Read buffer with reverse pipetting to avoid bubbles.
13. Read the plate immediately on the MSD SECTOR instrument.

Example 908 Co-Crystallography with p110α (Alpha)

N-terminally truncated p110α (alpha) was produced according to Chen et al and Nacht et al. (Chen, P., Y. L. Deng, S. Bergqvist, M. D. Falk, W. Liu, S. Timofeevski and A. Brooun "Engineering of an isolated p110alpha subunit of PI3Kalpha permits crystallization and provides a platform for structure-based drug design." (2014) Protein Sci 23(10):

1332-1340; Nacht, M. et al (2013) "Discovery of a potent and isoform-selective targeted covalent inhibitor of the lipid kinase PI3Kalpha." J. Med. Chem. 56(3): 712-721).

Standard protocols were applied to production of crystals in the presence of project compounds. Harvested crystals were preserved for diffraction data collection by immersion in liquid nitrogen and mounted on a synchrotron beamline producing monochromatic X-rays. Diffraction data were collected, reduced and merged using standard protocols. The crystallographic unit cells and space group were isomorphous with those reported previously (Nacht, 2013; Chen, 2014). Placement of project compounds into electron density maps and crystallographic refinement to resolution limits of between 2.36 and 2.56 Å were performed using standard protocols.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

We claim:

1. A process for the preparation of compound 8, having the structure:

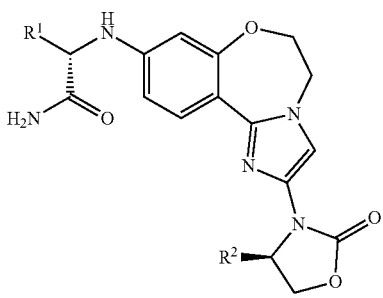

8 or a stereoisomer, geometric isomer, tautomer, or pharmaceutically acceptable salt thereof, wherein:
$R^1$ is selected from the group consisting of —$CH_3$, —$CH_2CH_3$, cyclopropyl, and cyclobutyl;
$R^2$ is selected from the group consisting of —$CH_3$, —$CHF_2$, —$CH_2F$, and —$CF_3$;
comprising reacting compound 7, having the structure:

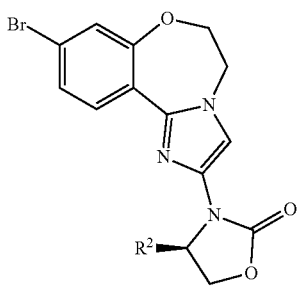

7 with an amino acid of formula $H_2NCH(R^1)CO_2H$ and a copper catalyst, followed by ammonium chloride, and HATU (1-[Bis(dimethylamino)methylene]-1H-1,2,3-triazolo[4,5-b]pyridinium 3-oxide hexafluorophosphate) to form 8.

2. The process of claim 1 wherein the copper catalyst to form 8 is CuI.
3. The process of claim 1 wherein $R^1$ is —$CH_3$.
4. The process of claim 1 wherein $R^2$ is —$CHF_2$.
5. The process of claim 1 wherein compound 8 has the structure:

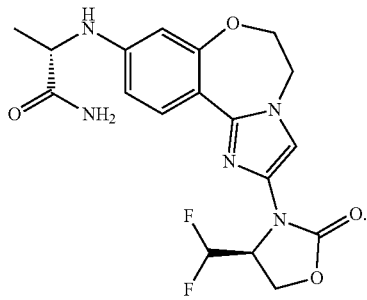 [SMILES: C[C@H](Nc1ccc2c(c1)OCCn1cc(N3C(=O)OC[C@H]3C(F)F)nc1-2)C(N)=O]

or pharmaceutically acceptable salt thereof.

6. The process of claim 1 wherein compound 7 is prepared by a process comprising reacting compound 6, having the structure:

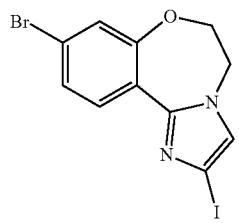

6 with a 4-substituted oxazolidin-2-one having the structure:

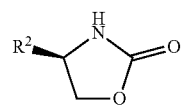

and a copper catalyst to form 7.

7. The process of claim 6 wherein the 4-substituted oxazolidin-2-one is (S)-4-difluoromethyloxazolidin-2-one.
8. The process of claim 6 wherein the copper catalyst to form 7 is selected from the group consisting of CuI and Cu(OAc)$_2$.
9. The process of claim 6 further comprising reacting compound 6, the 4-substituted oxazolidin-2-one, and the copper catalyst, with trans-N, N'-dimethyl-1,2-cyclohexane diamine.

* * * * *